(12) United States Patent
Castillo et al.

(10) Patent No.: US 12,415,978 B2
(45) Date of Patent: Sep. 16, 2025

(54) BIOREACTOR AND RELATED METHODS

(71) Applicant: UNIVERCELLS TECHNOLOGIES S.A., Nivelles (BE)

(72) Inventors: José Castillo, Brussels (BE); Bastien Mairesse, Uccle (BE); Sebastien Jean-Pierre Michel Rodriguez, Ecaussinnes-Lalaing (BE)

(73) Assignee: UNIVERCELLS TECHNOLOGIES S.A., Nivelles (BE)

( * ) Notice: Subject to any disclaimer, the term of this patent is extended or adjusted under 35 U.S.C. 154(b) by 90 days.

(21) Appl. No.: 18/143,302

(22) Filed: May 4, 2023

(65) Prior Publication Data
US 2023/0272324 A1    Aug. 31, 2023

Related U.S. Application Data

(63) Continuation of application No. 17/887,898, filed on Aug. 15, 2022, now Pat. No. 11,680,237, which is a
(Continued)

(51) Int. Cl.
*C12M 1/00* (2006.01)
*C12M 1/02* (2006.01)
(Continued)

(52) U.S. Cl.
CPC ............ *C12M 23/34* (2013.01); *C12M 23/42* (2013.01); *C12M 23/44* (2013.01); *C12M 25/18* (2013.01); *C12M 27/00* (2013.01); *C12M 27/18* (2013.01)

(58) Field of Classification Search
CPC ...... C12M 23/34; C12M 23/42; C12M 23/44; C12M 25/18; C12M 27/00; C12M 27/18
(Continued)

(56) References Cited

U.S. PATENT DOCUMENTS 5,266,476 A    11/1993   Sussman et al.
5,501,971 A *  3/1996   Freedman .............. C12M 23/34
                                          435/399
(Continued)

FOREIGN PATENT DOCUMENTS

CN    101294136 A    10/2008
CN    201258281 Y    6/2009
(Continued)

OTHER PUBLICATIONS

Xiao, et al.; Reviews of high thermal conductivity polymer dielectrics for electrical insulation; Tianjin University; China; 2015.
(Continued)

*Primary Examiner* — Michael L Hobbs
*Assistant Examiner* — Lenora A Abel
(74) *Attorney, Agent, or Firm* — Dickinson Wright PLLC; Andrew D. Dorisio

(57) ABSTRACT

An apparatus for culturing cells includes a bioreactor. The bioreactor may be modular and may include in a chamber a fixed bed, such as an unstructured or structured fixed bed (such as a spiral bed) for culturing cells, with a return column arranged centrally within the chamber. The modular bioreactor may include a plurality of structured fixed bed arranged in a stacked configuration. The modular bioreactor may include an outer casing forming a space for conditioning (e.g., insulating, heating, cooling) at least a chamber in which cells are cultured. The bioreactor may also include an impeller with radially curved blades, and may also suspend the impeller so that it may move from side-to-side and align with an external drive. Related methods are also disclosed.

20 Claims, 33 Drawing Sheets

Related U.S. Application Data continuation of application No. 16/955,904, filed as application No. PCT/EP2018/086394 on Dec. 20, 2018, now abandoned.

(60) Provisional application No. 62/758,152, filed on Nov. 9, 2018, provisional application No. 62/733,375, filed on Sep. 19, 2018, provisional application No. 62/608,261, filed on Dec. 20, 2017.

(51) Int. Cl.
 *C12M 1/12* (2006.01)
 *C12M 3/00* (2006.01)

(58) Field of Classification Search
 USPC .......................................... 435/293
 See application file for complete search history.

(56) References Cited

U.S. PATENT DOCUMENTS

| | | | |
|---|---|---|---|
| 6,372,495 | B1 | 4/2002 | Flendrig |
| 8,137,959 | B2 | 3/2012 | Castillo Fernandez |
| 8,986,979 | B2 | 3/2015 | Castillo |
| 9,399,755 | B2 | 7/2016 | Karerangabo |
| 2009/0017541 | A1 | 1/2009 | Kodama |
| 2011/0223582 | A1 | 9/2011 | Castillo et al. |
| 2011/0263021 | A1* | 10/2011 | Stobbe ................ F04B 43/0736 435/243 |

FOREIGN PATENT DOCUMENTS

| | | |
|---|---|---|
| CN | 103865958 A | 6/2014 |
| CN | 106635797 A | 5/2017 |
| KR | 20130109000 A | 10/2013 |
| KR | 10-2015-0111535 | 10/2015 |
| WO | 2010032260 A1 | 3/2010 |
| WO | 2014093439 A1 | 6/2014 |

OTHER PUBLICATIONS

Archambault, J. et al., Development of Bioreactors for the Culture of Surface Immobilized Plant Cells, Biochemical Engineering Research Unit, Chemical Engineering Department, McGill University, Biotechnology and Bioengineering, vol. 35, Mar. 1990, pp. 1-10, Montreal, Canada.

Ozturk, et al.; "Cell Culture Technology for Pharmaceutical and Cell-Based Therapies"; Taylor Francis Group; Florida; 2006.

Scheper; "Advances in Biochemical Engineering/Biotechnology"; Recent Progress of Biochemical and Biomedical Engineering in Japan II; 2004.

Evoqua Water Technologies; "Biosphere Moving Bed Biological Systems"; Biosphere; www.evoqua.com.

\* cited by examiner

BIOREACTOR AND RELATED METHODS

This application is a continuation of U.S. Utility application Ser. No. 17/887,898 filed on Aug. 15, 2022 which is a continuation of U.S. application Ser. No. 16/955,904 filed on Jun. 19, 2020, which is a national stage of International Patent Application PCT/EP2018/086394, which claims the benefit of U.S. Provisional Application Ser. Nos. 62/758,152, 62/733,375 and 62/608,261, all of which are incorporated herein by reference.

TECHNICAL FIELD

This document relates generally to the cell culturing arts and, more particularly, to a bioreactor and related methods.

SUMMARY

An objective of this disclosure is to provide a bioreactor, which may be in modular form, that utilizes one or more structured fixed beds to promote case of manufacturing and use, while still achieving excellent cell culturing outcomes from the resulting homogeneity and repeatability afforded, even when scaled up or down.

According to a first aspect of the disclosure, an apparatus for culturing cells in connection with a fluid flow, comprising a modular bioreactor including a fixed bed for culturing cells.

In some embodiments, the modular bioreactor comprises a base portion having a first chamber, an intermediate portion forming at least part of a second, outer chamber for receiving the fixed bed and at least part of a third inner chamber for returning fluid flow from the second outer chamber to the first chamber, and a cover portion for positioning over the intermediate portion. The fixed bed may comprise a structured fixed bed, and the intermediate portion may comprise a tubular part, the structured fixed bed extending spirally around the tubular part, or the intermediate portion may comprise an inner wall of the fixed bed. In any embodiment, the intermediate portion may comprise a plurality of intermediate parts, each associated with a structured fixed bed.

In some embodiments, at least one of the plurality of intermediate parts is perforated for allowing fluid to flow from a first structured fixed bed below the at least one intermediate part to a second structured fixed bed above the at least one intermediate part. In some embodiments, each of the plurality of intermediate parts is tubular, and each structured fixed bed comprises a spiral bed wound around the tubular intermediate part. A perforated support may be provided for the structured fixed bed.

In some embodiments, the intermediate portion may further comprise a tubular casing for forming a periphery of the modular bioreactor. The tubular casing forms a space for heating, cooling, or insulating the bioreactor. The intermediate portion may comprise a plurality of intermediate parts, each adapted for connecting with each other.

In some embodiments, the intermediate portion includes a tube for engaging at least one intermediate part and forming an inner wall of the outer second chamber for receiving the fixed bed. The tub may engage wherein the tube engages a first intermediate part below the tube and a second intermediate part above the tube. The second intermediate part may include openings for creating a fluid film along the third inner chamber. Supports, such as vertical rods, may be provided for supporting the second intermediate part from the first intermediate part.

In some embodiments, the cover portion comprises a removable cap including a plurality of ports. The removable cap may have an outer diameter that is less than an outer diameter of the intermediate portion. At least one of the ports may include a threaded metal insert. The cover portion may have an outer diameter that is equal to or greater than an outer diameter of the intermediate portion.

The intermediate portion may comprise an intermediate part adapted for positioning at least partially within the base portion. The intermediate part may further include a flow disruptor for disrupting fluid flow.

The base portion may include a further chamber radially outward of the first chamber in fluid communication with the second outer chamber including the fixed bed. This further chamber may be formed by an upstanding wall having a plurality of openings for transmitting fluid from the first chamber to the further chamber.

In some embodiments, an agitator is associated with the base portion. The intermediate portion may be adapted for suspending the agitator in the first chamber in a manner that allows side-to-side movement for alignment with an external drive.

In some embodiments, a container is provided for containing the agitator, the container including a central inlet and a plurality of radially oriented outlets. A flow divider may be associated with the central inlet. In any embodiment, or as an independent component separate from any bioreactor, the agitator may comprise a plurality of curved blades.

In some embodiments, a plurality of flow disruptors are provided for dividing the fluid flow entering the third inner chamber into a plurality of streams. The plurality of flow disruptors may be associated with a ring. In some embodiments, one or more conduits for permitting gas to enter into a space behind one of the streams. The one or more conduits may be connected to a structure including the plurality of flow disruptors. For example, a first conduit may be connected to the structure, or both first and second conduits may be connected to the structure. Alternatively, the first and second conduits may not be connected to the structure.

According to a further aspect of the disclosure, an apparatus for culturing cells is disclosed. The apparatus comprises a modular bioreactor comprising a base portion removably connected to both a central column and an outer casing, the outer casing and central column together forming a compartment for culturing cells.

In some embodiments, the compartment includes at least one structured fixed bed. The compartment may include a plurality of structured fixed beds, arranged in a stacked configuration. An intermediate part, such as a screen, may be positioned between at least two of the plurality of structured fixed beds.

In some embodiments, the at least one structured fixed bed comprises a spiral bed. Each of the plurality of stacked, structured fixed beds is wrapped around the central column. The central column comprises first and second interconnected tubes, a first structured fixed bed of the plurality of structured fixed beds being wrapped around the first tube and a second structured fixed bed of the plurality of structured fixed beds being wrapped around the second tube. The central column comprises first and second tubes for engaging a perforated support extending between at least two of the plurality of structured fixed beds.

In any embodiment, the structured fixed bed may comprise a cartridge adapted for being inserted into and removed from the second, outer chamber or compartment.

According to a further aspect of the disclosure, a bioreactor for culturing cells is provided. The bioreactor may comprise a base part having a first chamber including an agitator for agitating a fluid. A first central column may be attached to the base part, optionally removably, the first central column forming at least part of a second, outer chamber for culturing cells and a third inner chamber for returning fluid flow from the second outer chamber to the first chamber.

In this or other embodiments, the second, outer chamber includes a first structured fixed bed. In this or any embodiment, the first structured fixed bed comprises a spiral bed, and may be wound or wrapped around the first central column. A second central column may also form at least part of the second outer chamber, and further including a second structured fixed bed spaced vertically from the first structured fixed bed. A perforated support may be provided between the first structured fixed bed and the second structured fixed bed.

In any embodiment, the second, outer chamber includes an unstructured bed.

According to yet another aspect of the disclosure, a bioreactor for culturing cells in connection with a fluid is disclosed. The bioreactor comprises a first chamber including an agitator for agitating the fluid, a second, outer chamber including a plurality of stacked beds for culturing cells, and a third, inner chamber for returning fluid from the second outer chamber to the first chamber.

In some embodiments, the bioreactor comprises a base portion having the first chamber, an intermediate portion forming at least part of the second, outer chamber and at least part of the third inner chamber, and a cover portion for positioning over the intermediate portion. In this or other embodiments, the intermediate portion comprises a first support for supporting a first bed of the plurality of stacked beds. The intermediate portion comprises a second support for supporting a second bed of the plurality of stacked beds, and may be adapted for removably connecting with the base portion and the cover portion.

In some embodiments, the second, outer chamber is bounded by an outer wall. The bioreactor may further include an outer casing forming a space with the outer wall, the space being for insulating, heating, or cooling the second, outer chamber.

Still another aspect of the disclosure pertains to a bioreactor for culturing cells in connection with a fluid. The bioreactor comprises a first chamber including an agitator for agitating the fluid, a second, outer chamber including at least one bed for culturing cells, and a third, inner chamber for returning fluid from the second outer chamber to the first chamber. The second, outer chamber may be bounded by an outer wall, and further including an outer casing forming a space with the outer wall, the space being for insulating, heating, or cooling the second, outer chamber.

In this or any other embodiments, the at least one bed comprises a structured fixed bed, such as a spiral bed, but could also be an unstructured bed. The inner chamber may be formed by at least one tube (which may be separate from or part of the bed). The least one tube may be connected to first and second supports bounding the at least one bed. The first and second supports may be connected to the outer wall, or the first and second supports may be at least partially perforated.

Yet another portion of the disclosure pertains to an apparatus for culturing cells, comprising a bioreactor including an agitator, the bioreactor adapted for maintaining the agitator in a suspended condition that allows side-to-side movement for alignment with an external drive.

In some embodiments, the bioreactor includes a base portion for receiving the agitator, and an intermediate portion for supporting a carrier for carrying the agitator in the suspended condition. The carrier may comprise a clip for engaging the intermediate portion.

A further aspect of the disclosure relates to an apparatus for culturing cells. The apparatus comprises a bioreactor including an agitator having a plurality of curved blades. The agitator may include a central open region radially inward of the plurality of curved blades, and may include one or more magnets.

This disclosure also relates to bioreactor comprising first and second stacked, structured beds. The bioreactor may further include a screen engaging both the first and second stacked, structured beds. The first and second stacked beds may comprise structured beds, such as spiral beds.

Also disclosed is a bioreactor including a structured fixed bed forming a central column of the bioreactor. The structured fixed bed may comprise a spiral bed. An inner surface of the structured fixed bed is fluid-impervious, such that a central column is formed for returning fluid to recirculation through the structured fixed bed, such as from top to bottom. The bioreactor may be modular, and a plurality of stacked, structured fixed beds may be provided, possibly with a gap or spacer between each bed in the stack.

According to still a further aspect of the disclosure, a method of manufacturing a bioreactor is provided. The method includes connecting a base portion including a first chamber with an agitator for agitating a fluid to at least one intermediate portion forming at least portion of a second, outer chamber for culturing cells in connection with fluid transferred from the second, outer chamber, and a third, inner chamber for returning fluid to the first chamber of the base portion.

In some embodiments, the method includes the step of connecting a cover portion over the at least one intermediate portion. The method may further include the step of spirally wrapping a matrix material around the intermediate portion to form a structured fixed bed for culturing cells in the outer chamber, or inserting a structured fixed bed into the second, outer chamber. The method may further include providing an outer casing to form a periphery of the second, outer chamber, or connecting the outer casing to the base portion. A further step involves stacking a plurality of structured fixed beds in the second, outer chamber, or providing a perforated support between the plurality of structured fixed beds. In any embodiment, the method may include the step of suspending the agitator above the base portion in a manner that permits side-to-side movement to align with an external drive.

Yet another aspect of the disclosure is a method of manufacturing a bioreactor, comprising providing a plurality of structured fixed beds in the bioreactor. The method may further include the step of providing a perforated spacer between each of the plurality of structured fixed beds. The method may further include the step of providing an inner tube along an inner side of each structured fixed bed and an outer tube along an outer side of each structured fixed bed. Still further, the method may include the step of providing a casing radially outward of the outer tube, the casing creating a space for insulating, heating, or cooling the bioreactor.

BRIEF DESCRIPTION OF THE DRAWING FIGURES

The novel features of the disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

FIG. 1 is a perspective view of a first embodiment of a bioreactor according to the disclosure.

FIGS. 2A, 2B, and 2C illustrate a possible environment of use of the bioreactor of FIG. 1.

Figure 14:
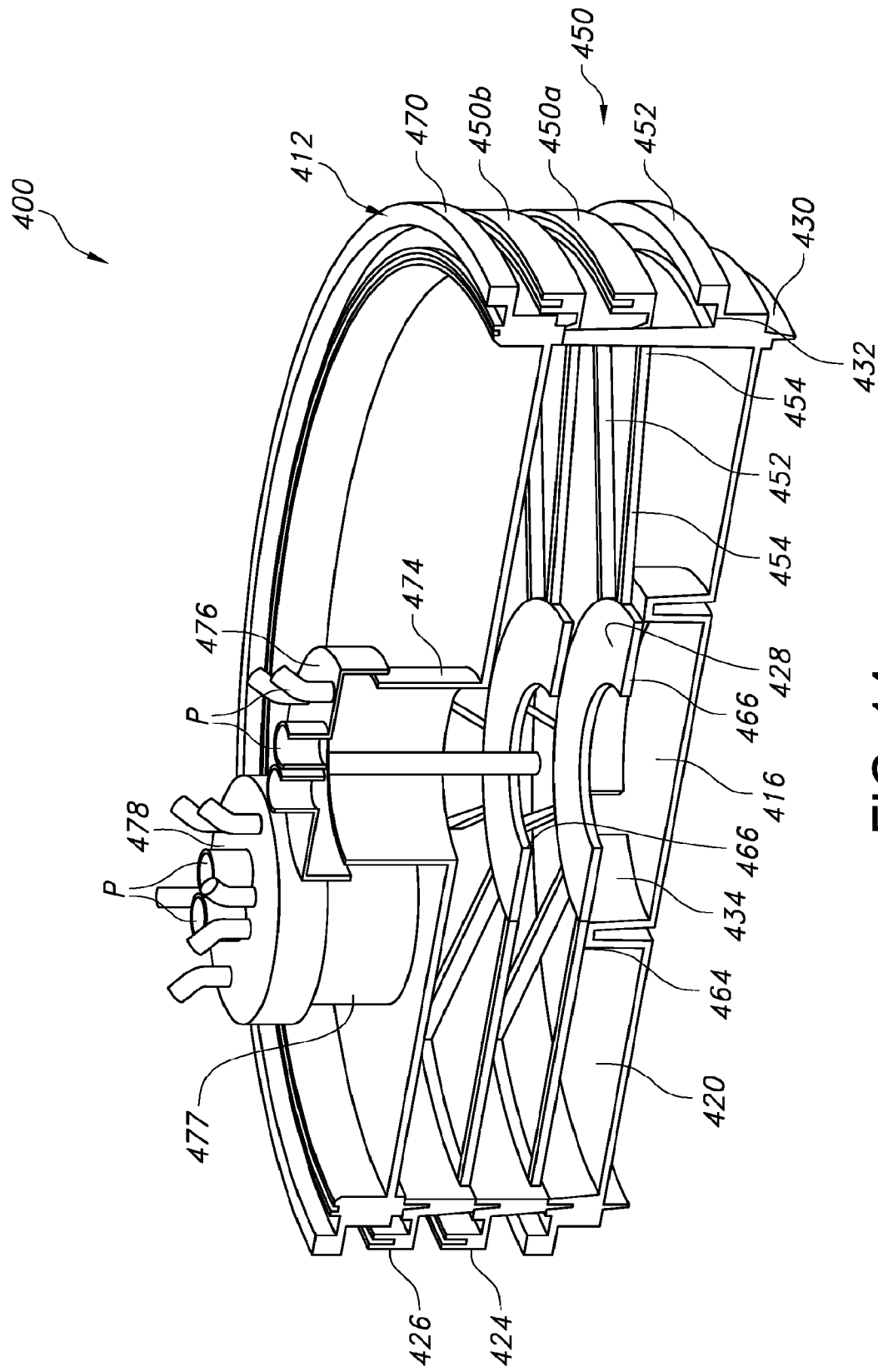
FIG. 14 is a cross-sectional view of a fourth embodiment of a bioreactor according to the disclosure.
Figure 16:
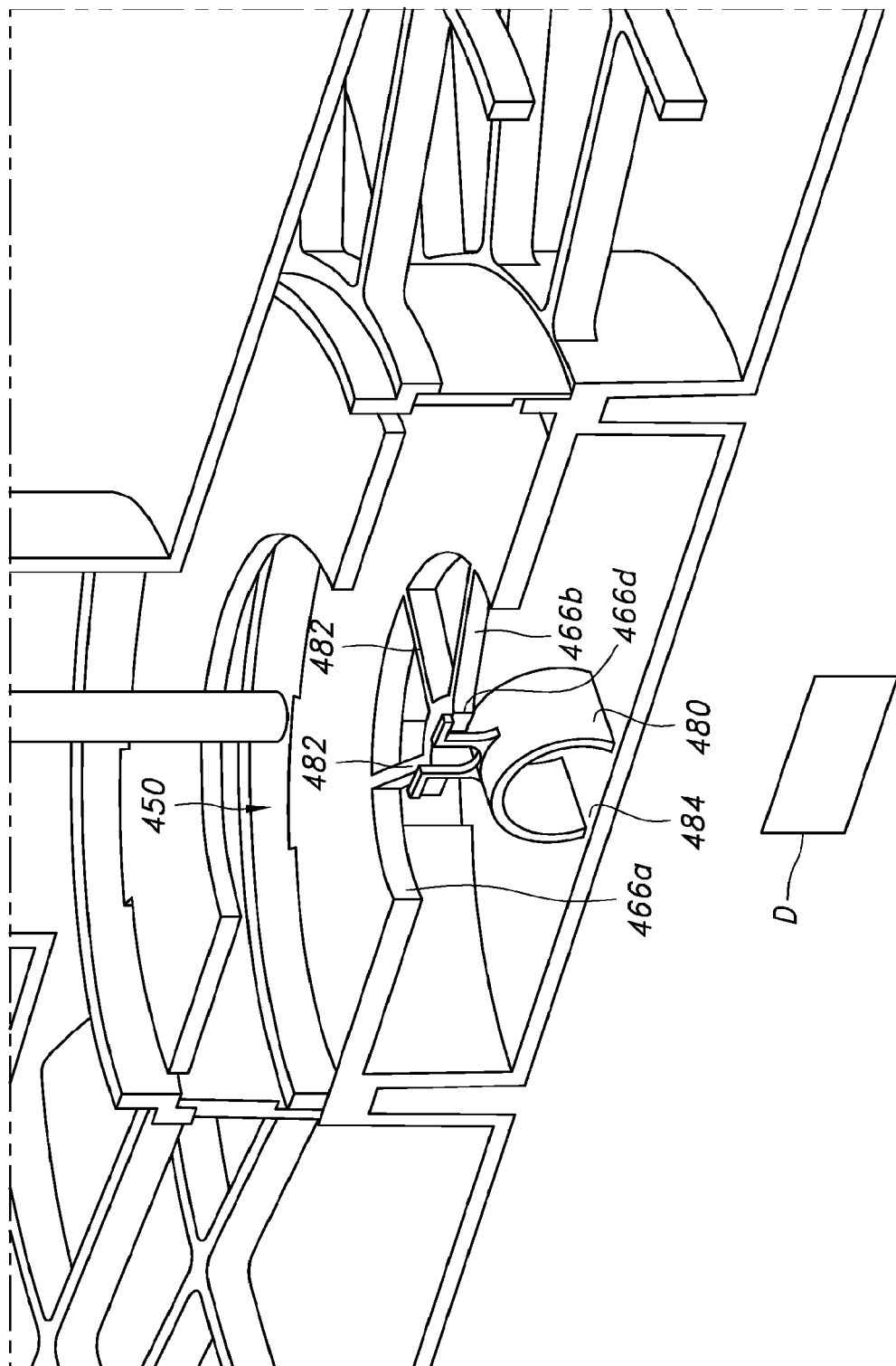
FIG. 16 is a partially cutaway view of portion of the bioreactor of FIG. 14.
Figure 16A:
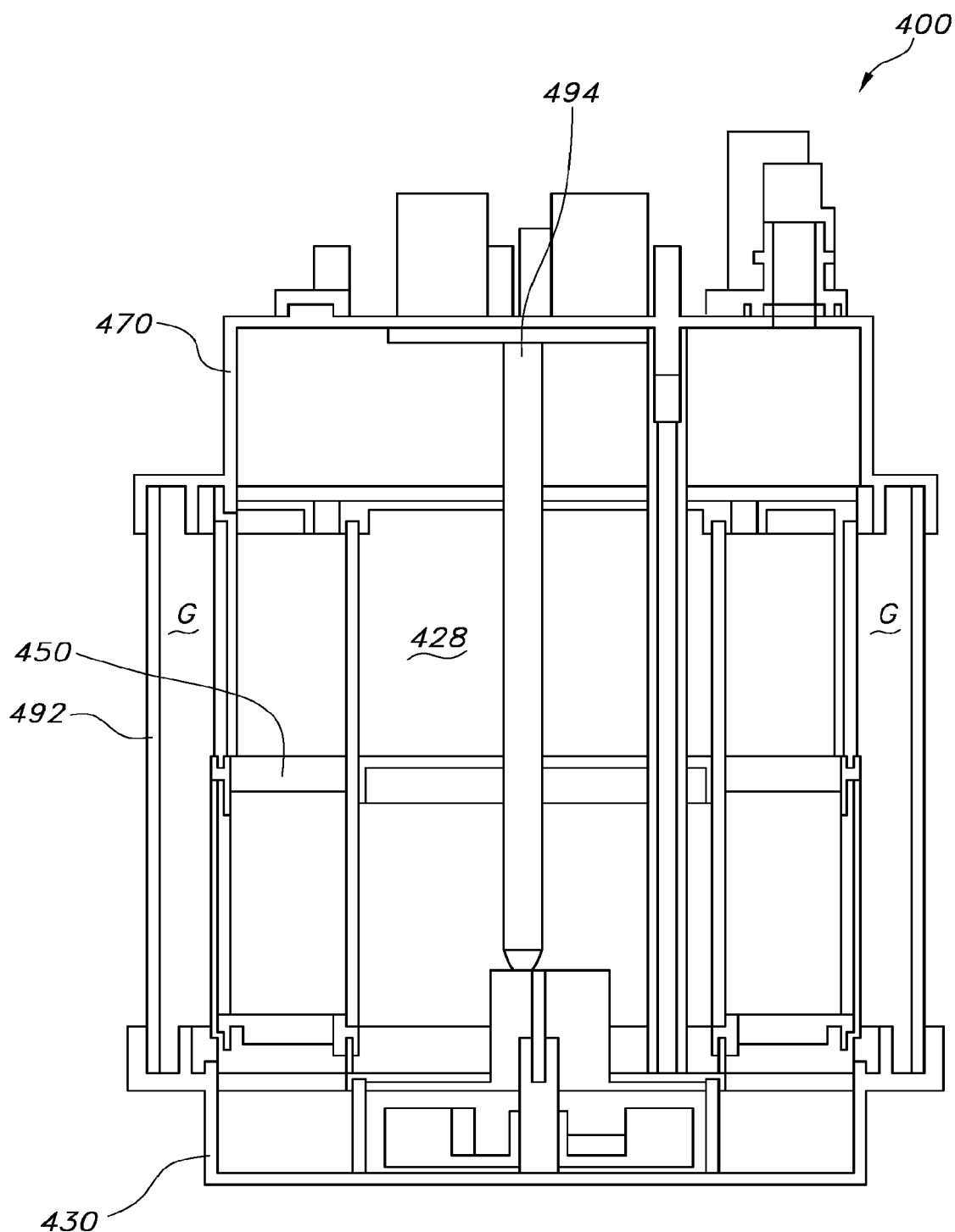
Figure 16B:
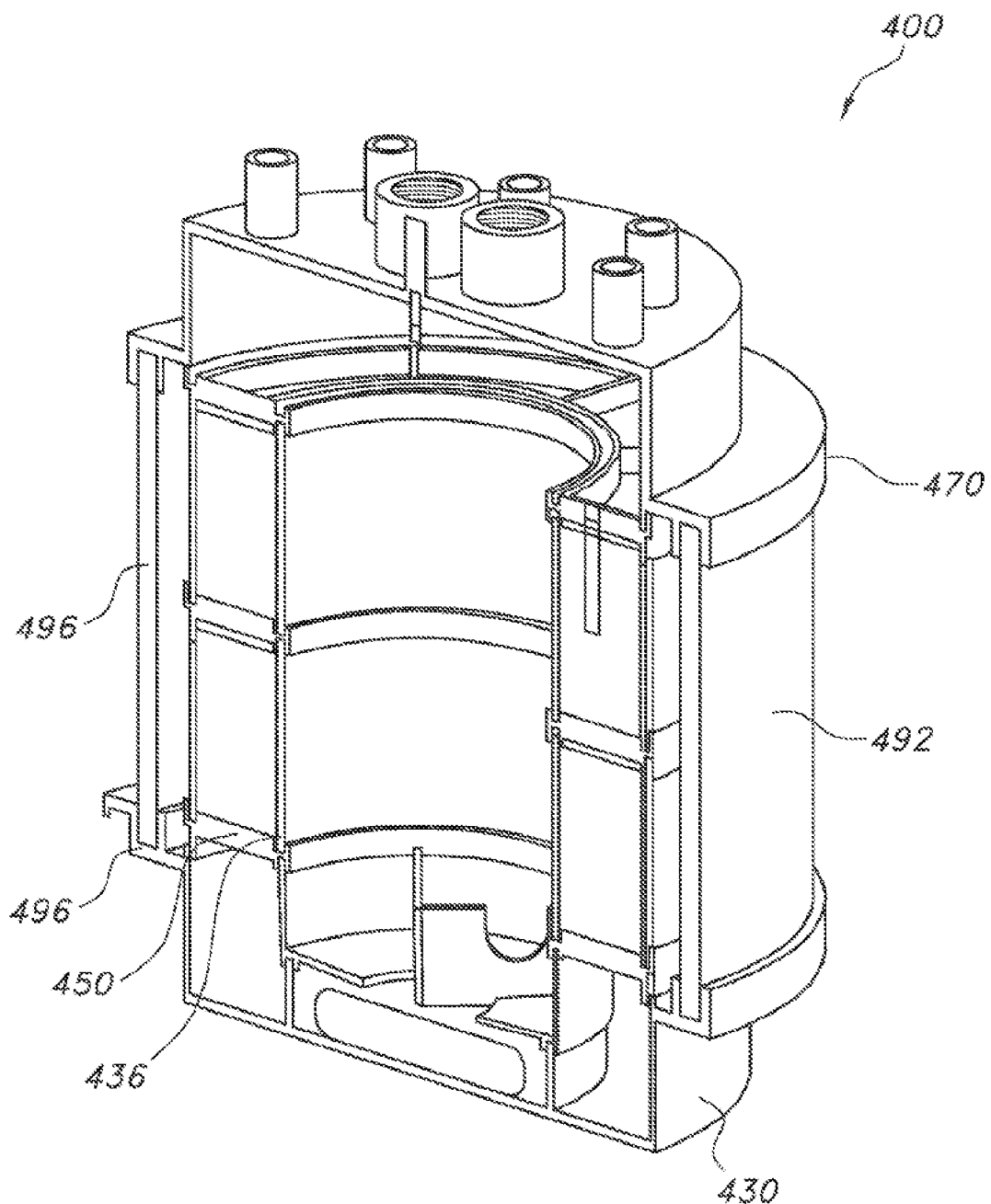
Figure 16C:
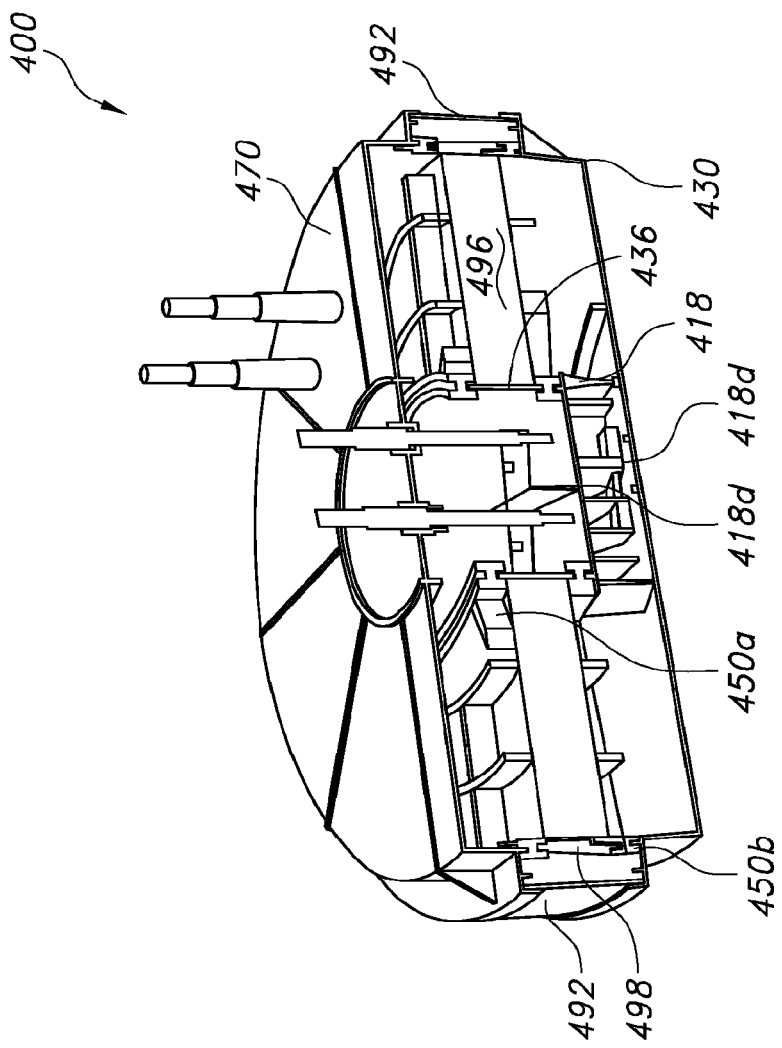

FIGS. 16A, 16B, and 16C are a cross-sectional views of further embodiments of the bioreactor of FIG. 14.

Figure 17:
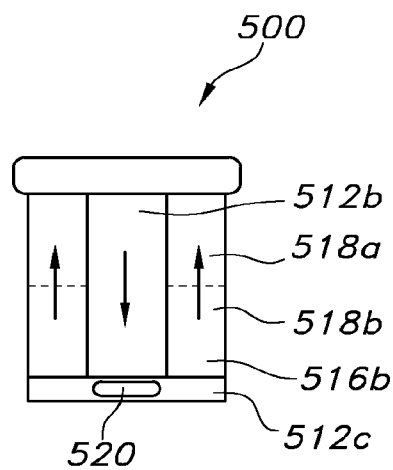
Figure 18:
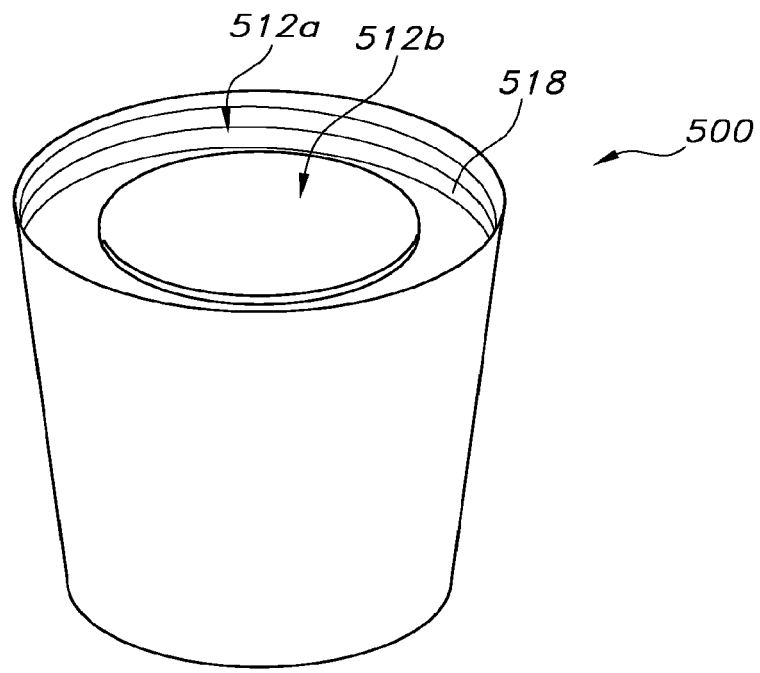

FIGS. 17 and 18 are schematic views of a fifth embodiment of a bioreactor according to the disclosure.

Figure 19:
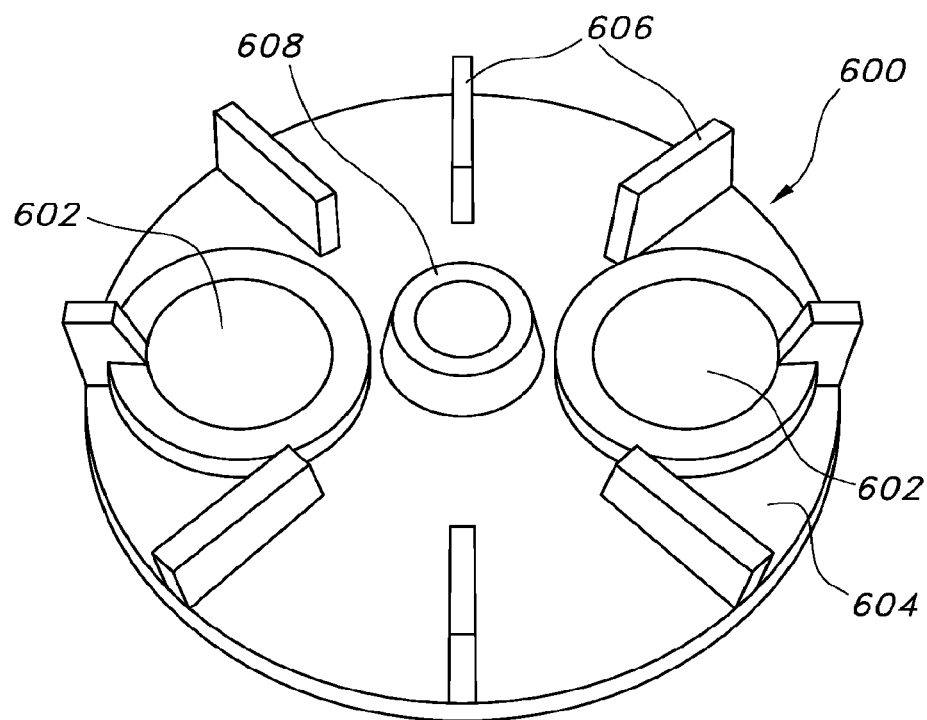
Figure 20:
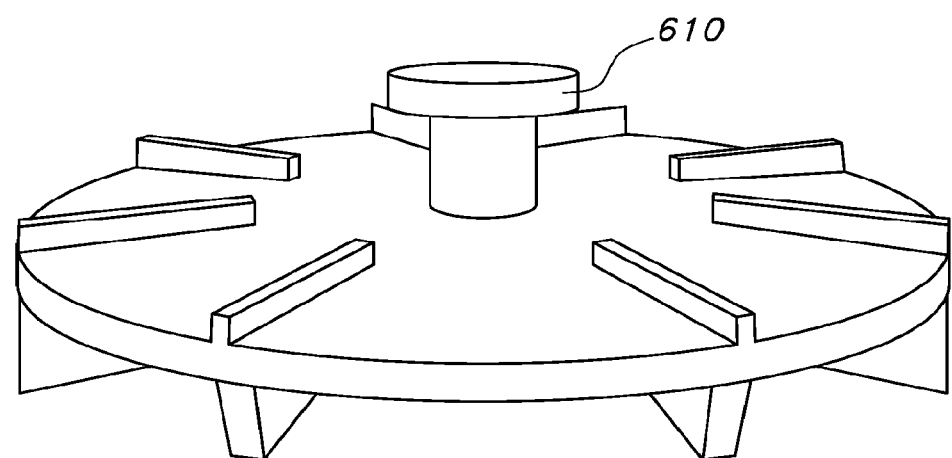

FIGS. 19 and 20 are bottom and top views of an embodiment of an impeller.

Figure 21:
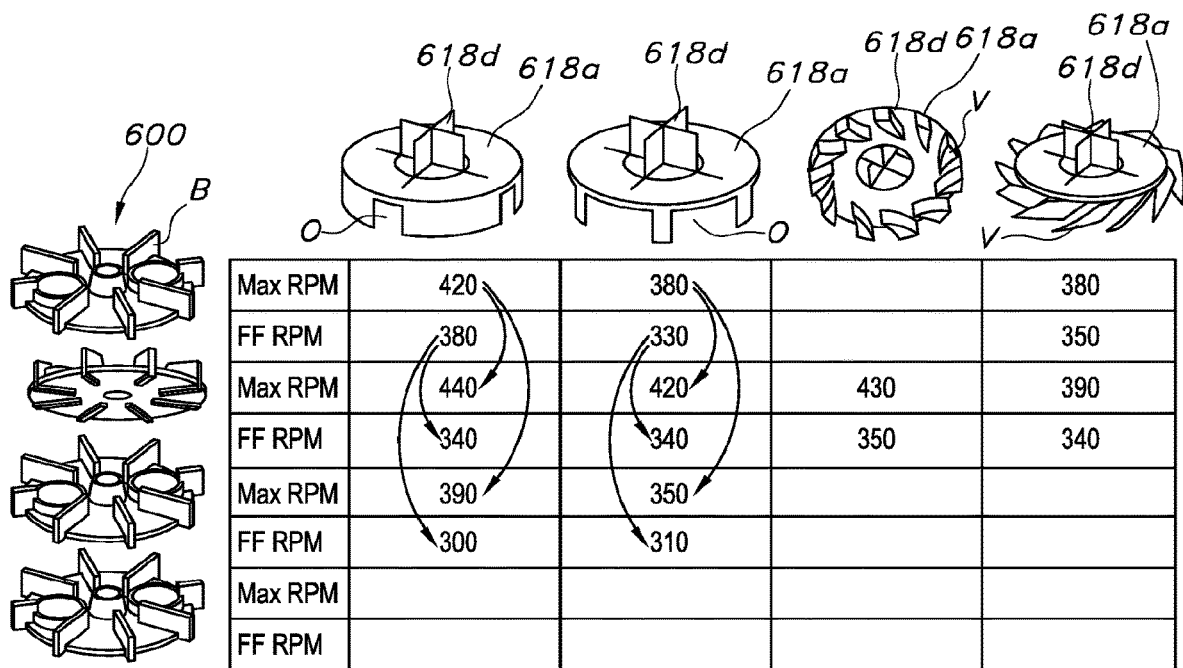

FIG. 21 is an illustration of various forms of impellers and associated housings.

Figure 22:
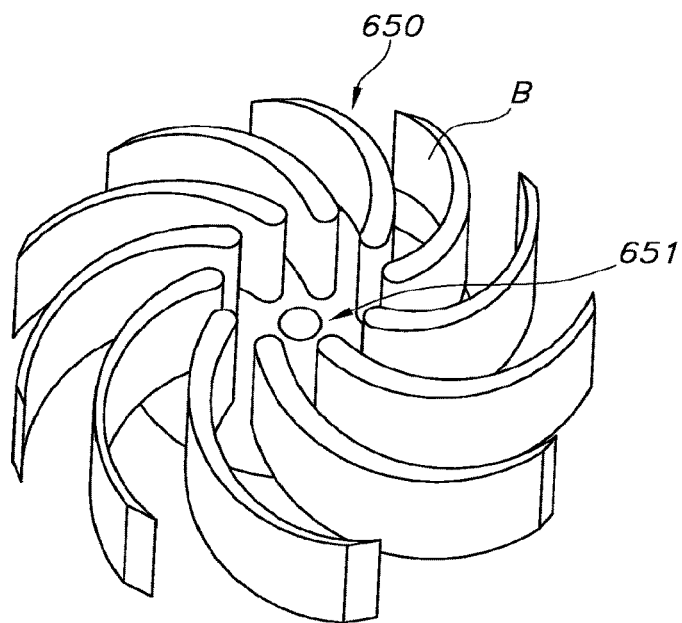

FIG. 22 is top view of another impeller according to the disclosure.

Figure 23:
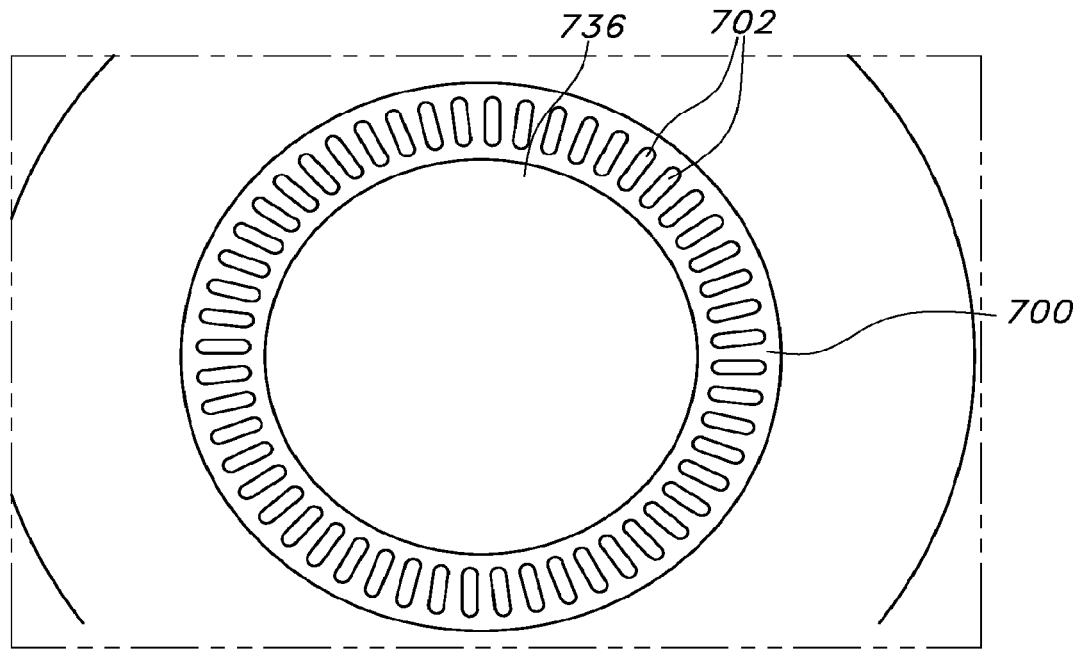
Figure 24:
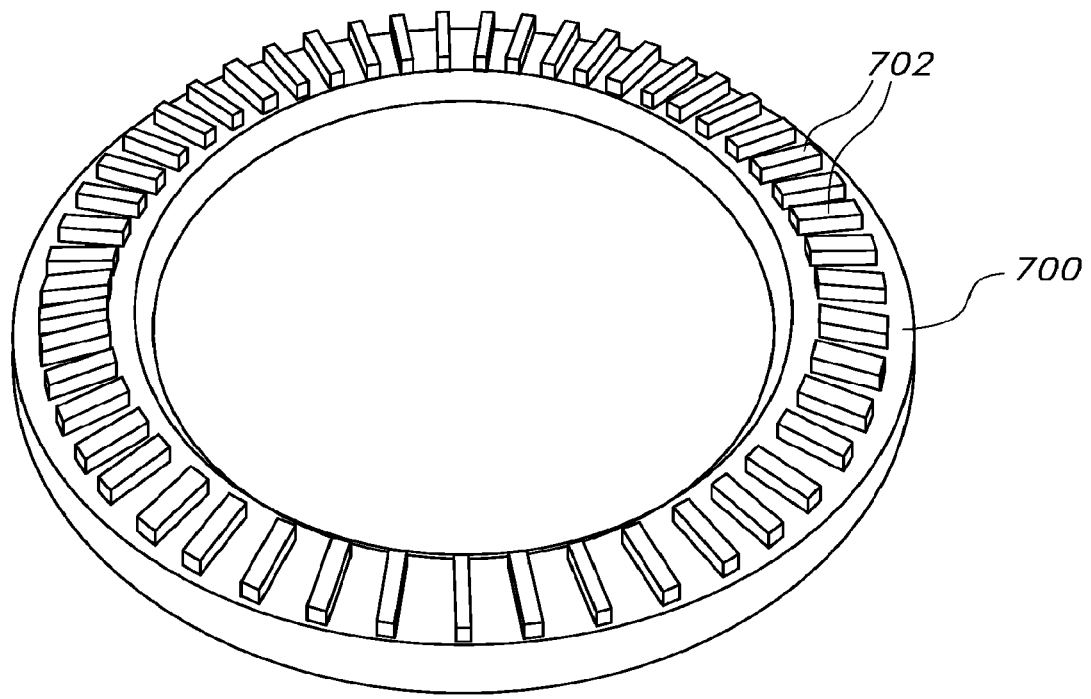

FIGS. 23 and 24 illustrate an embodiment of a flow disruptor.

Figure 25:
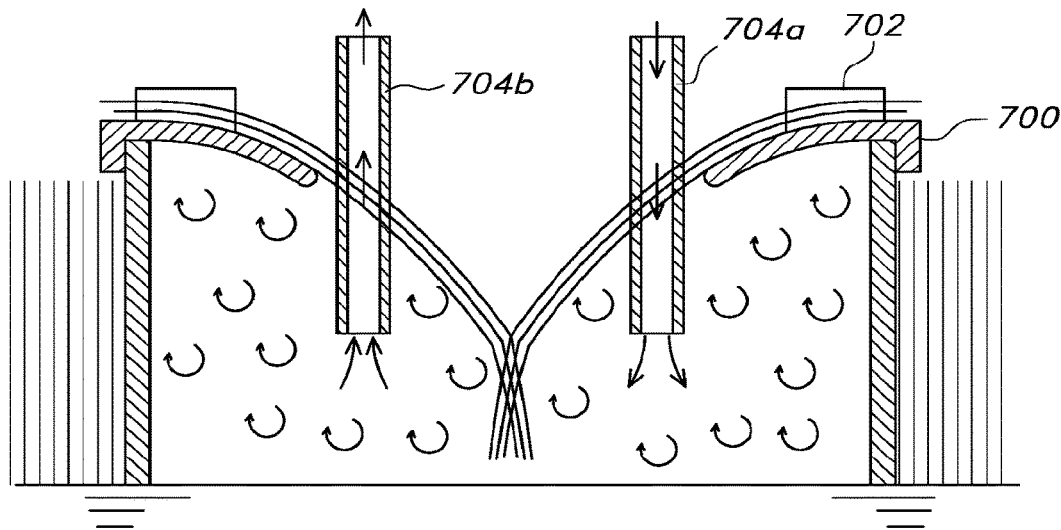
Figure 26:
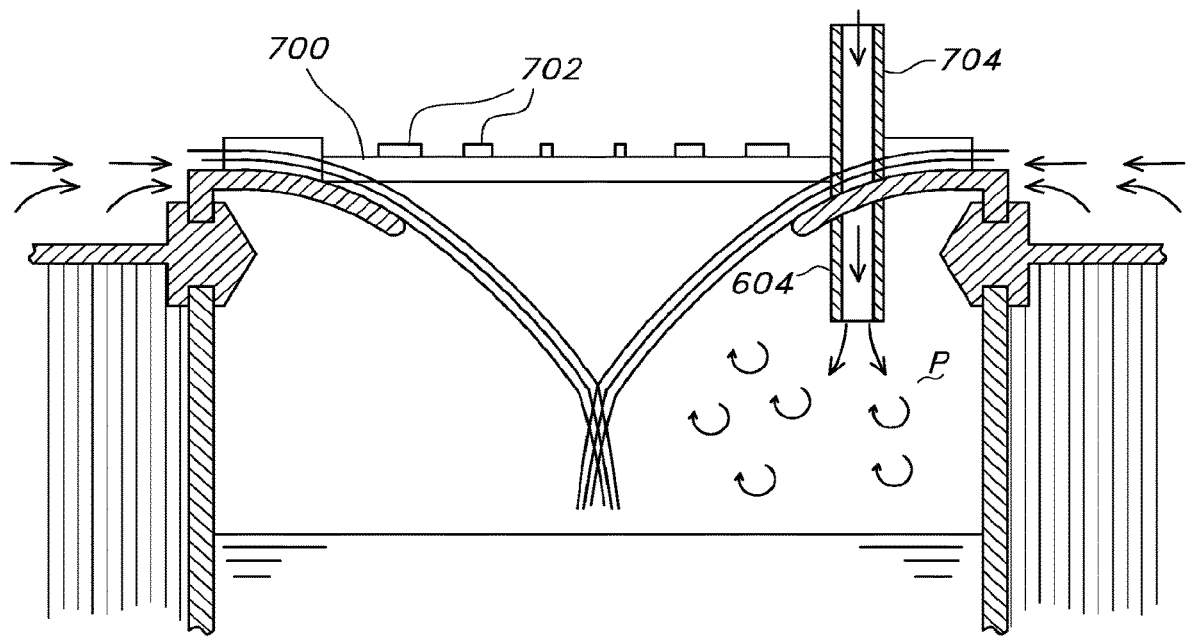

FIGS. 25 and 26 illustrate the use of conduits for supplying a gas to a portion below a "waterfall" of a bioreactor.

Figure 27:
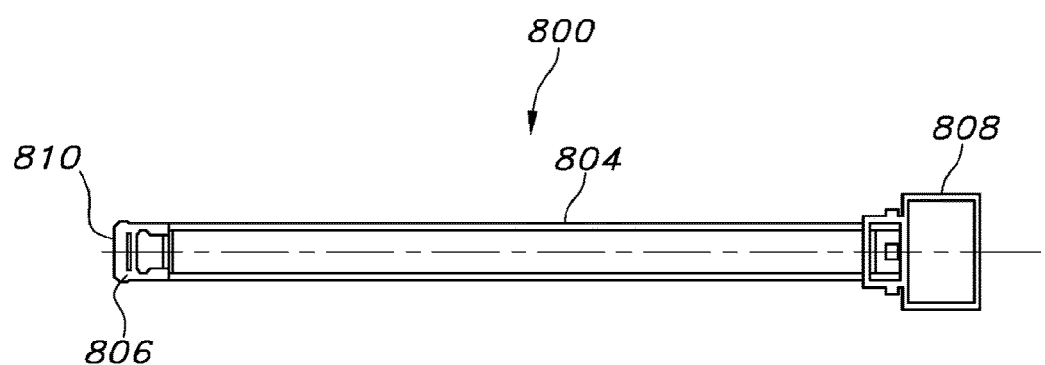
Figure 28:
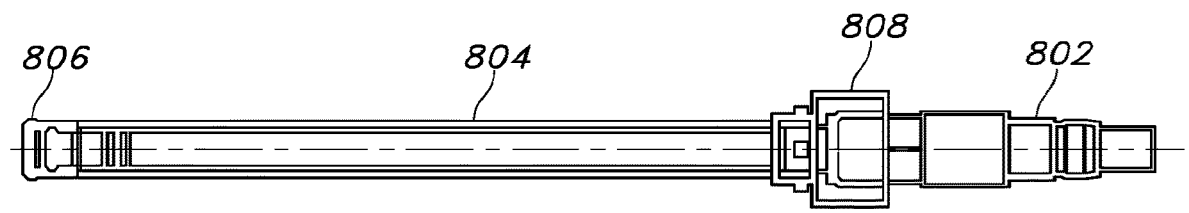

FIGS. 27 and 28 illustrate embodiments of a probe for use in connection with a bioreactor.

Figure 29:
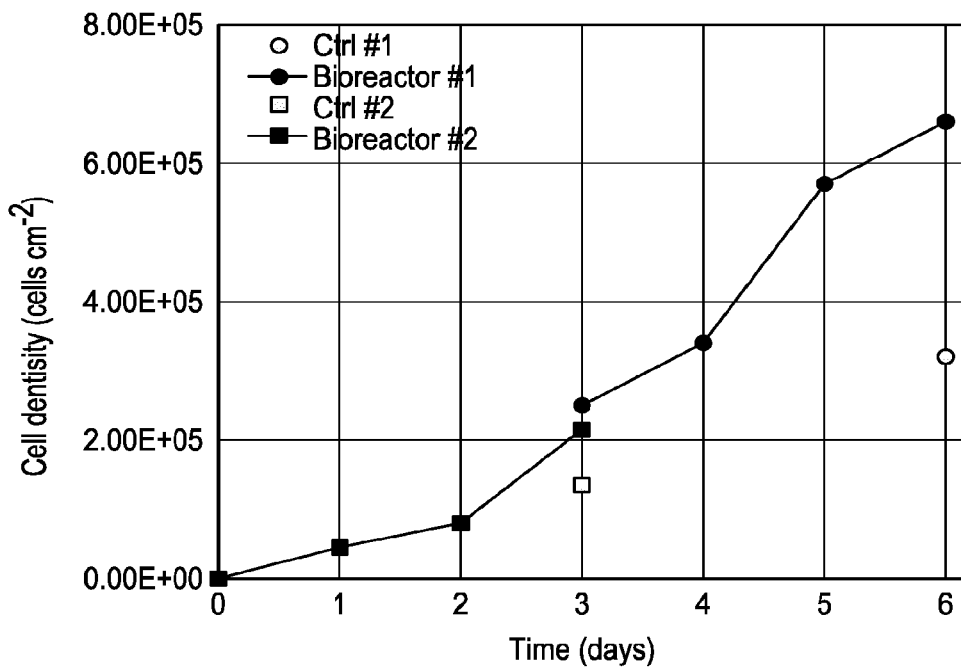
Figure 30:
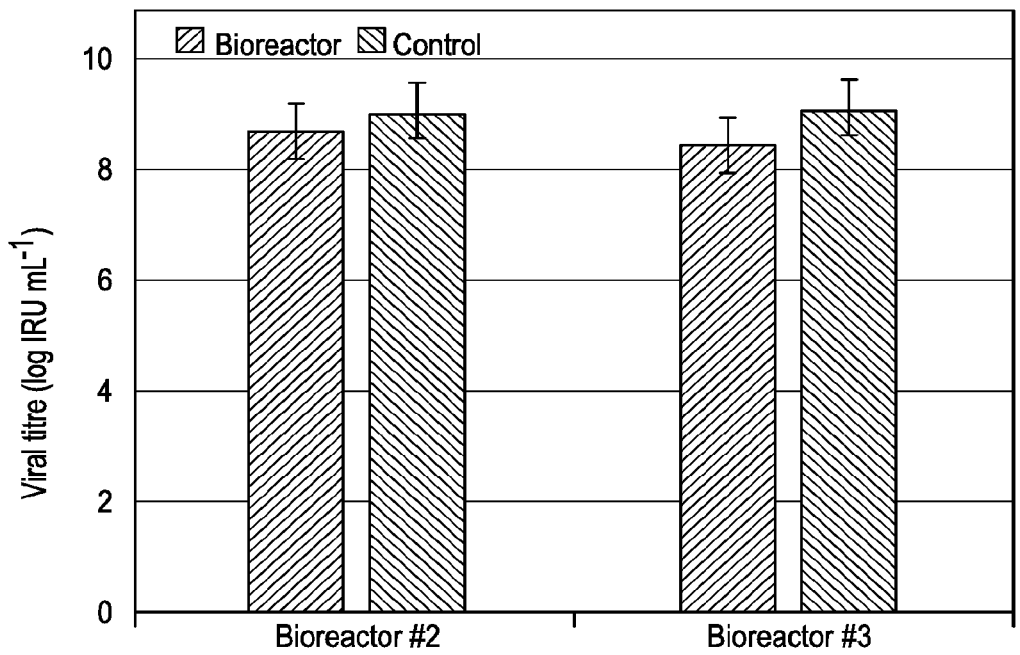

FIGS. 29 and 30 are graphs illustrating testing of the bioreactor.

Figure 31:
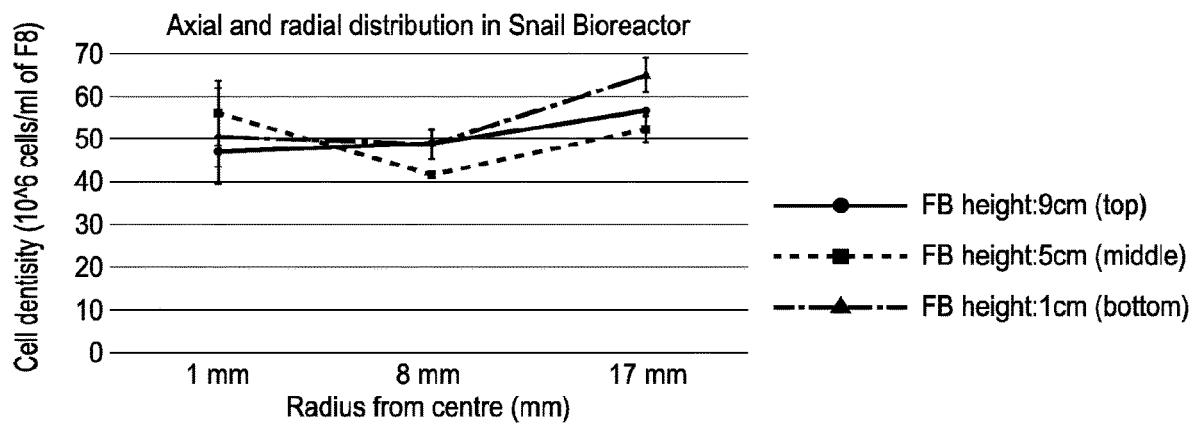
Figure 32:
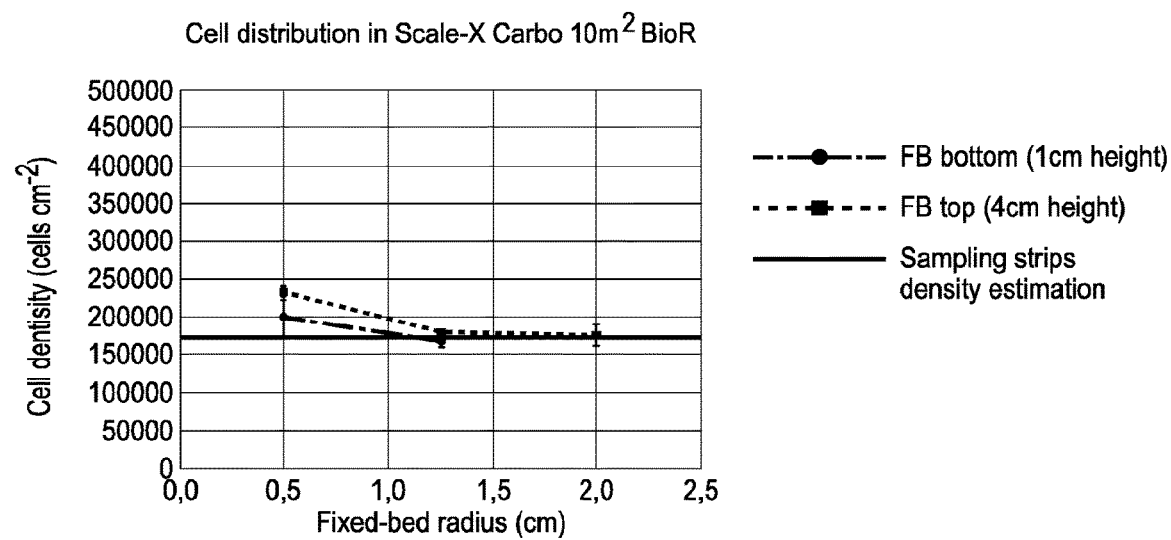
Figure 33:
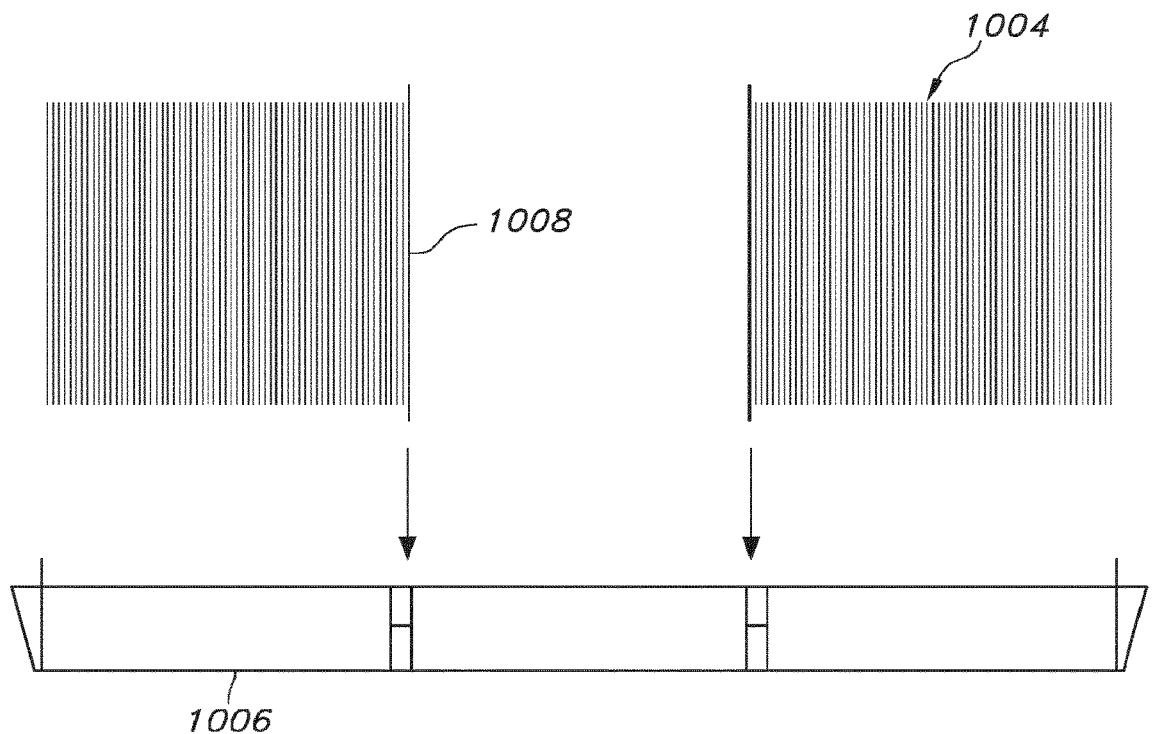
Figure 34:
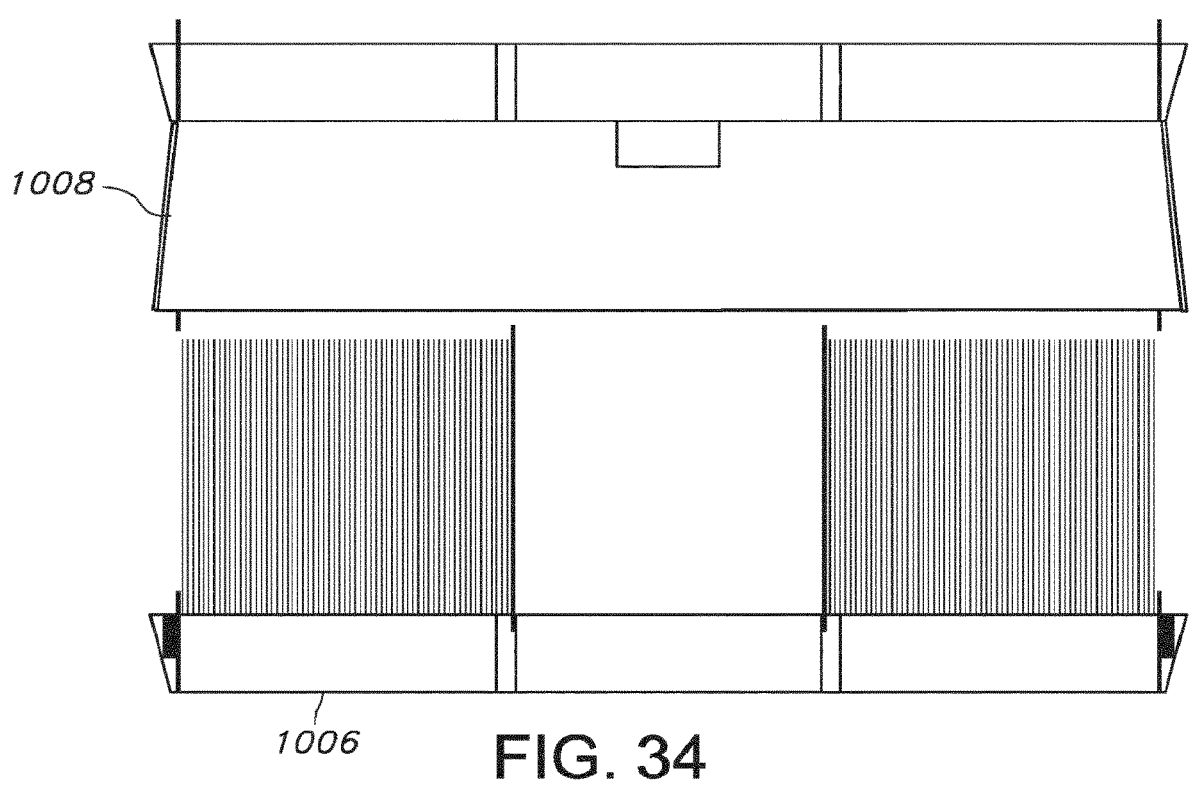
Figure 35:
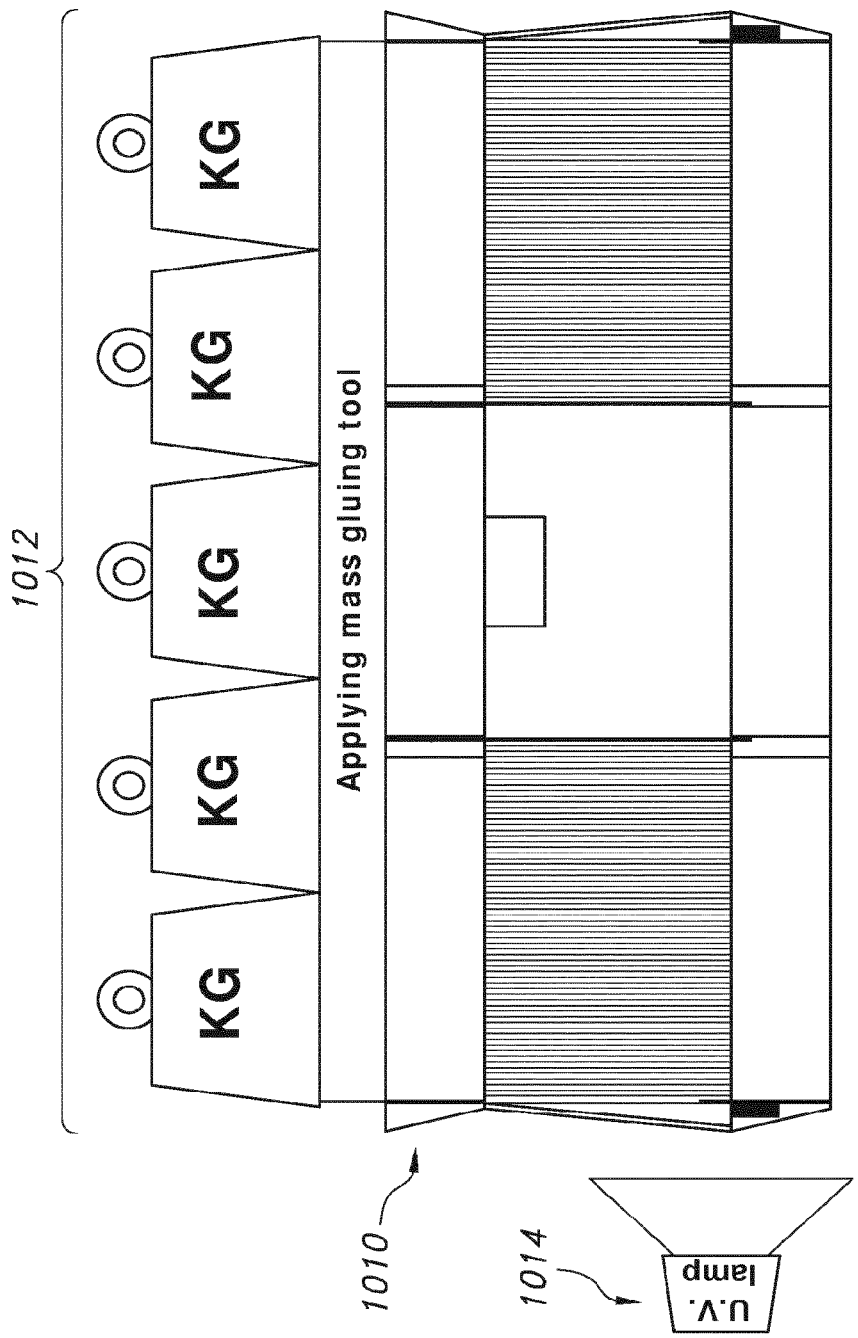

FIGS. 31 and 32 are graphs illustrating testing of the bioreactor to assess cell density of structured fixed beds in a stacked configuration.

FIGS. 33, 34, 35, 36, 37, and 38 schematically illustrate a method of manufacturing a modular bioreactor according to the disclosure.

DETAILED DESCRIPTION

Bioreactors are frequently used for culturing cells. Typical bioreactors are constructed with fixed dimensions (height, in particular), and thus can be difficult and costly to transport to remote locations where cell cultures may be needed for providing treatments (particularly, the developing world). The fixed nature also prevents past bioreactors from being adapted for a variety of uses.

A further issue relates to the ability of maximizing cell density for a given area. Many past proposals for bioreactors use fluidized beds. While such beds may work well for promoting cell growth and provide certain advantages, the resulting volume of space in the bioreactor required to create such a bed is large. Readily scaling a bioreactor with an unstructured or fluidized bed while achieving the desired cell growth is also challenging, and there is a current demand for bioreactors that may be utilized in a variety of operating conditions in the field (including, for example, within a sterile hood, where clearance may be limited).

Accordingly, a need is identified for an improved bioreactor that would be easy to deliver and assemble, particularly at remote locations, and/or would be readily adaptable for use in a variety of sizes or configurations, or for different applications or uses. In some embodiments of the disclosure, the present disclosure concerns systems and methods for the production of biologics. In particular, the production of cells, viruses or cells- or virus-derived products.

In some embodiments, a bioreactor disclosed herein allows for high density cell growth. For example, density of at least 2 million cells/ml, at least 5 million cells/ml, at least 10 million cells/ml, at least 20 million cells/ml, at least 40 million cells/ml, at least 60 million cells/ml, or at least 100 million cells/ml. In some embodiments, the density can reach 300, 250 or 200 million cells/ml. In some embodiments, the bioreactor disclosed herein can have a total volume of at least 1 L, at least 10 L, at least 30 L, at least 40 L, or at least 50 L. In some embodiments, the bioreactor total volume can be at most 2500 L, at most 200 L, at most 150 L, at most 100 L, or at most 75 L. By bioreactor total volume reference can be made to the total liquid volume that can be introduced in the bioreactor, which will then be full.

In some embodiments, the bioreactor can be a perfusion bioreactor, wave bioreactor, cylindrical bioreactor, bag bioreactor, moving bed bioreactor, packed bed bioreactor, fibrous bioreactor, membrane bioreactor, batch bioreactor, or continuous bioreactor. In some embodiments, the bioreactors can be made from or comprise a suitable material, for example, stainless steel, glass, aluminum, or plastic. In some embodiments, the bioreactor can allow for downstream analysis of products. In some embodiments, a bioreactor described herein can be connected with or to one or more inactivation units to inactivate for example a produced product (e.g. virus), a concentrator, or a purification unit. In some embodiments, a concentrator is a device suited for reducing the volume of the liquid in which target biomolecule resides. In some embodiment, the concentrator comprises a tangential flow filter or a dead-end filter. In some embodiment, the concentrator is based on filtration and/or size exclusion chromatograph. In some embodiments, the concentrator can be a filtration device, a micro-filtration device, or an ultra-filtration device or a combination of both micro- and ultra-filtration device. In some embodiments, a purification unit described herein can comprise a filtration device, an ultrafiltration device, a difiltration device, a pH adjustment device, a centrifugation device, a washing device, a chromatography column (e.g. affinity chromatography, ionic exchange chromatography, hydrophobic interaction chromatography, size exclusion chromatography, or immune-affinity chromatography), a chromatography membrane, a harvest device, a dialysis device, a concentration device, or any combination thereof.

Access to a bioreactor described herein can be via a lid, or door. In some embodiments, an access mechanism for the bioreactor can comprise for example, a lock and key mechanism, a pass code punch pad, card swipe, transponder reader, finger print scanner, retina scanner, sensors, automatic identification and data capture methods such as radio-frequency identification (RFID), biometrics (like iris or facial recognition system), magnetic stripes, Optical character recognition (OCR), smart cards, voice recognition, or any other access mechanism.

In some embodiment, a bioreactor disclosed herein can comprise a process controller. In some embodiments, the process controller is configured to control operations of a bioreactor and can include a plurality of sensors, a local computer, a local server, a remote computer, a remote server, or a network. In some embodiments, the bioreactor can include one or more sensors, for example, a temperature sensor (e.g., a thermocouple), flow rate sensor, gas sensor, or any other sensor. In some embodiments, the process controller can be operational to control aspects of a product manufacturing process, and can be coupled to sensors disposed in the bioreactor, for example, to control the temperature, volume flow rate or gas flow rate into the bioreactor in real time. In some embodiments, a process controller can include a display, for example, a computer monitor, a smart phone app, a tablet app, or an analog display, that can be accessed by a user to determine the state of the system. In some embodiments, the process controller can include an input, for example, a keyboard, a key pad, a mouse, or a touch screen, to allow a user to enter control parameters for controlling the operation of the bioreactor. In some embodiments, the process controller can control access to the bioreactor.

In some embodiments, the bioreactor disclosed herein can comprise and or contain sensors for monitoring different parameters. In some embodiments, a sensor disclosed herein can be located in any compartment of a bioreactor disclosed herein. In some embodiment, sensors described herein can be a gas sensor (e.g. oxygen, nitrogen, or carbon dioxide), pH sensor, temperature sensor, cell density sensor, or dissolved oxygen sensor. In some embodiments, the sensors disclosed herein can measure amongst other things, biomass or cell density, the dissolved oxygen partial pressure, oxygen content, the $p$TI value, the temperature, certain concentrations of nutriments, such as lactate, ammonium, carbonates, glucose or any metabolic product or product to be metabolized which could for example reflect the cell density. In some embodiment, cell density (biomass density) can be determined by electrical impedance analysis or electrical impedance spectroscopy using an arrangement of measuring electrode. In some embodiments, a bioreactor according to the disclosure can comprise sensors for measuring culture parameters. In some embodiments, a sensor disclosed herein can be in contact with culture medium in the bioreactor. In some embodiments, culture parameters can comprise amongst other things, the dissolved oxygen partial pressure, the pH, the temperature, the optical density, certain concentrations of nutriments, such as lactate, ammonium, carbonates, glucose or any metabolic product or product to be metabolized which could for example reflect the cell density. In some embodiment, a bioreactor disclosed herein can use regulation loops according to the disclosed parameters. In some embodiments, a regulation loop can for example, modulate the quantity of oxygen to be injected according to the value of the dissolved oxygen partial pressure present or the quantity of dissolved oxygen consumed by the cells; speed of circulation of the culture medium; inject $CO_2$ according to the pH value obtained by the sensors or any other type of regulation generally used in this type of culture. In some embodiments, cells can be exposed to dissolved oxygen concentrations of 300 µM or less (160 mmHg partial pressure), less than 200 µM, or between 20 and 150 µM. In some embodiments, cells can be exposed to about 0%, 1%, 5%, 10%, 20%, 30%, 40%, 50%, 60%, 70%, 78%, 80%, 90%, or 100% nitrogen and/or about 0%, 1%, 5%, 10%, 21%, 30%, 40%, 50%, 60%, 70%, 80%, 90% or 100% oxygen. In some embodiments, cells can be exposed to pure oxygen or an oxygen enriched atmosphere.

In some embodiments, a bioreactor disclosed herein may comprise heating and/or cooling devices, designed to heat and/or cool culture medium. In some embodiments, the heating device can be an electrical element, an electrical coil or any other heating means generally used in the field of cell culture, such as for example a thermostatically controlled double jacket. In some embodiments, cooling device may be any suitable cooling devices such as a Peltier element. In some embodiments, with regard to the culture medium and gas, the bioreactor comprises at least one inlet for the introduction of gas and/or culture medium and at least one outlet for the collection of the culture medium contained in the bioreactor. In some embodiments, mix of gas or gaseous mixture and culture medium can be supplied to through the same supply line.

In some embodiments, culture medium can be circulated via an agitator. In some embodiments, and agitator can be a rotatable, non-contact magnetic impeller, a blade or screw agitation system, or an external circulation system. In some embodiments, the agitator can comprise a disk blade turbine, a curved blade turbine, an open lade fluid foil axial impeller, a turbine impeller with pitched blades, or a three-blade propeller. In some embodiments, the agitator can have a flow rate of less than about 0.01 l/min, 0.05 l/min, 0.1 l/min, 0.5 l/min, 1 l/min, 2 l/min, 5 l/min, 10 l/min, 15 l/min, 20 l/min, 50 l/min, 100 l/min, or 150 l/min to more than about 160 l/min, 180 l/min, 200 l/min, or 250 l/min.

In some embodiments, the bioreactor described herein comprises a fixed bed. In some embodiments, the fixed bed is a structured fixed bed (which means that it is formed of an easily replicated, generally homogeneous, substantially fixed structure, and thus is not randomly oriented or unstructured, and, as can be appreciated, could take a variety of sizes or shapes while meeting this qualification). In some embodiments, the structured fixed bed described herein can provide for a large cell growth surface within a small volume while still allowing circulation of medium and cells. In some embodiments, the structured fixed bed described herein can comprise a tortuous path for cells and cell culture media. In some embodiments, a spacer layer facilitates the tortuous path. In some embodiments, the structured fixed bed can comprise one or more cell immobilization layers having a surface which allows cells to adhere and grow upon and forming a cell immobilization section. In some embodiments, adjacent to the cell immobilization layers are one or more spacer layers. In some embodiments, the spacer layer can include a structure which forms a spacer section. In some embodiments, the spacer section allows passage of cells and medium through an open but tortuous path. In some embodiments, the structure or nature of the spacer layers can be chosen such that the spacer layers create a tortuous, open path for cells and culture media to travel in parallel to the surface of said spacer and cell immobilization layers. In some embodiments, the tortuous path or channel formed by the spacer section creates turbulence which facilitates cell and cell medium incursion into the immobilization layers.

In some embodiments, the spacer layer can be a mesh or comprises a mesh structure. In some embodiments, mesh structure or mesh can be a structure comprising a network or web-like pattern of filament, wire or thread. In some embodiments, the network can define pores, openings or perforations formed of a three-dimensional weave. In some embodiments, the spacer layers and/or the cell immobilization layers of a spacer section and a immobilization section can be made of a biocompatible polymer, for example polyester, polyethylene, polypropylene, polyamide, plasma treated polyethylene, plasma treated polyester, plasma treated polypropylene or plasma treated polyamide. In some embodiments, the spacer layer or the cell immobilization layer can comprise silica, polystyrene, agarose, styrene divinylbenzene, polyacrylonitrile or latex. In some embodiments, the layers can be hydrophilic or hydrophobic. In some embodiments, the cell immobilization layer can be hydrophilic. In some embodiments, a cell immobilization layer can be woven or nonwoven. In some embodiments, a cell immobilization section and a spacer section can be alternately positioned. In some embodiment, alternately positioned sections can alternate in a vertical position or in a horizontal position. In some embodiments, one or more layers of cell immobilization layers can be superimposed on one or more spacer layers (or vice versa). In some embodiments, a structured bed disclosed herein can be tightly or loosely rolled to a structure such as a spiral structure or varying shape.

Figure 1:
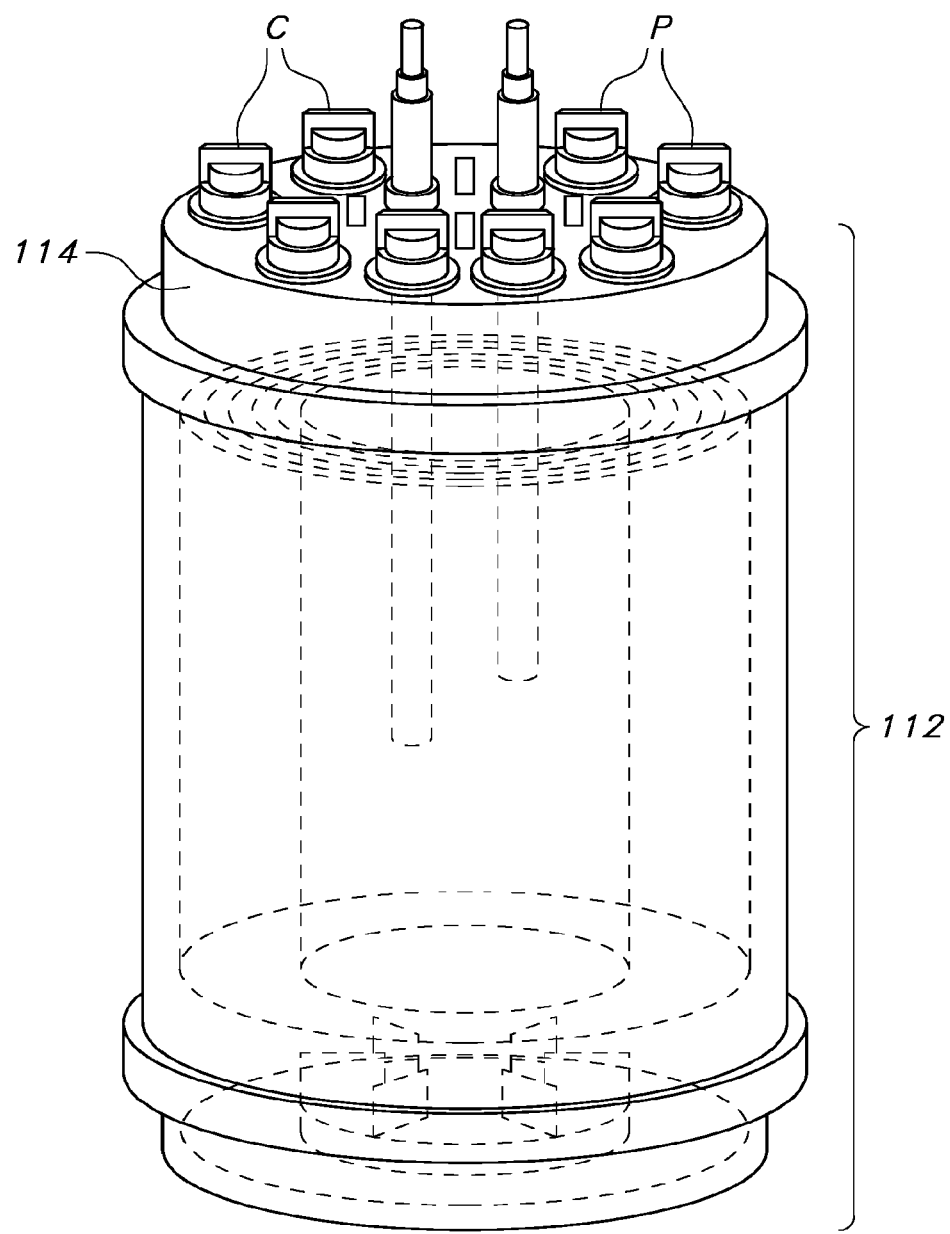
Figure 2C:
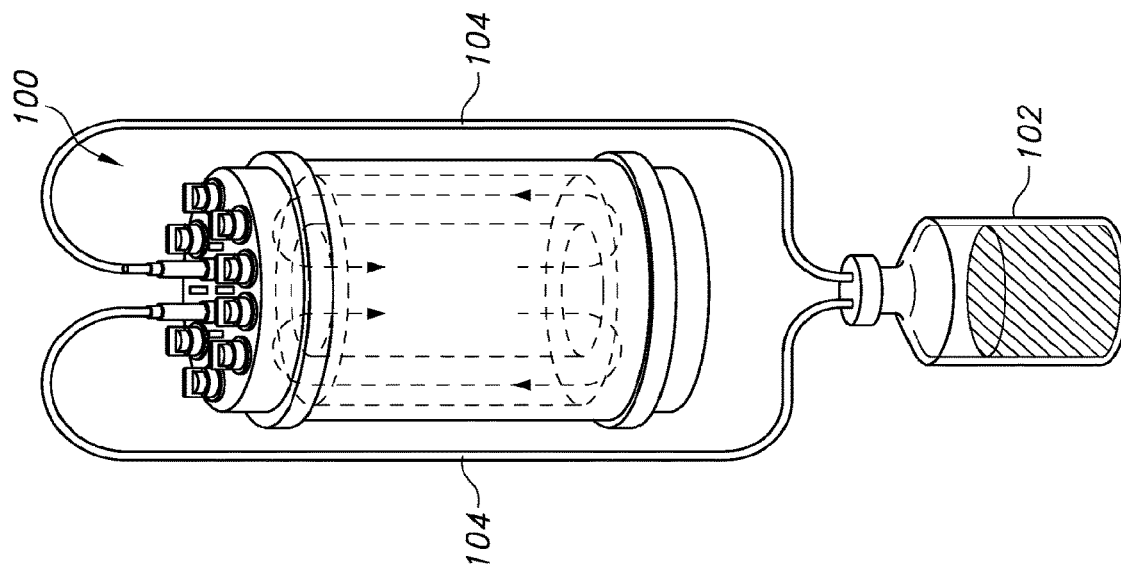
Figure 2B:
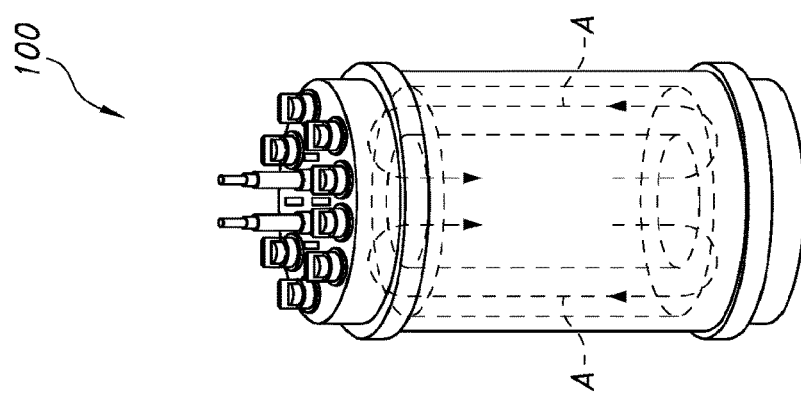
Figure 2A:
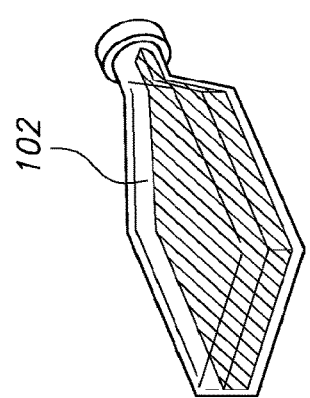
Figure 3:
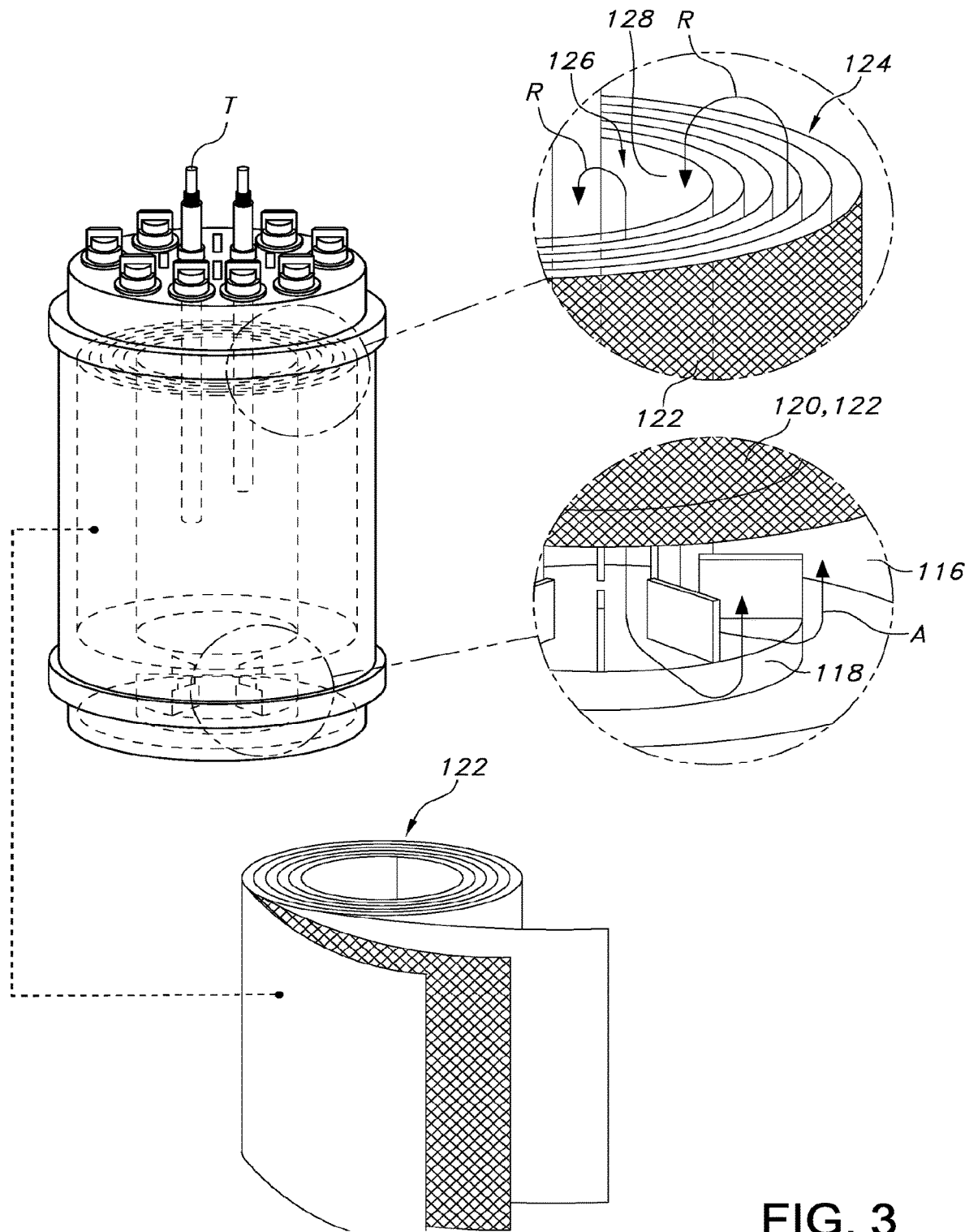
FIG. 3 is a perspective view of the bioreactor of FIG. 1, including several enlarged views.

Reference is now made to FIGS. 1-3, which illustrate one embodiment of a bioreactor 100 for culturing cells, according to one aspect of the disclosure. In some embodiments, the bioreactor 100 includes an external casing or housing 112 forming an interior compartment and a removable cover 114 for covering the interior compartment, which may include various openings or ports P with removable covers or caps C for allowing for the selective introduction or removal of fluid, gas (including by way of a sparger), probes, sensors, samplers, or the like. As indicated in FIGS. 2A, 2B, and 2C, in some embodiments, the bioreactor 100 may be used in connection with an external reservoir 102 and conduits 104 (e.g., forward and return) to form a continuous loop for circulating fluid to the bioreactor 100.

Within the interior compartment formed by the bioreactor housing 112, several compartments or chambers may be provided for transmitting a flow of fluid or gasses throughout the bioreactor 100. As indicated in FIG. 3, in some embodiments, the chambers may include a first chamber 116 at or near a base of the bioreactor 100. In some embodiments, the first chamber 116 may include an agitator for causing fluid flow within the bioreactor 100. In some embodiment, the agitator may be in the form of a "drop-in" rotatable, non-contact magnetic impeller 118 (which as outlined further below may be captured or contained within a container (not shown) including a plurality of openings for admitting and releasing fluid). In some embodiments, as a result of the agitation provided, fluid may then flow upwardly (as indicated by arrows A in FIG. 2) into an annular chamber 120 along the outer or peripheral portion of the bioreactor 100. In some embodiments, the bioreactor is adapted to receive a fixed bed, such as a structured spiral bed 122, which in use may contain and retain cells being grown. As indicated in FIG. 3, in some embodiments, the spiral bed 122 may be in the form of a cartridge that may be dropped or placed into the chamber 120 at the point of use. In some embodiments, the spiral bed 122 can be pre-installed in the chamber during manufacture at a facility prior to shipping.

In some embodiments, fluid exiting the chamber 120 is passed to a chamber 124 on one (upper) side of the bed 122, where the fluid is exposed to a gas (such as oxygen or nitrogen). In some embodiments, fluid may then flow radially inwardly to a central return chamber 126. In some embodiments, the central return chamber can be columnar in nature and may be formed by an imperforate conduit or tube 128 or rather formed by the central opening of the structured spiral bed. In some embodiments, the chamber 126 returns the fluid to the first chamber 116 (return arrow R) for recirculation through the bioreactor 100, such that a continuous loop results ("bottom to top" in this version). In some embodiments, a sensor, for example a temperature probe or sensor T may also be provided for sensing the temperature of the fluid in the chamber 126. In some embodiments, additional sensors (such as, for example, pH, oxygen, dissolved oxygen, temperature) may also be provided at a location before the fluid enters (or re-enters) the chamber 116.

Figure 3A:
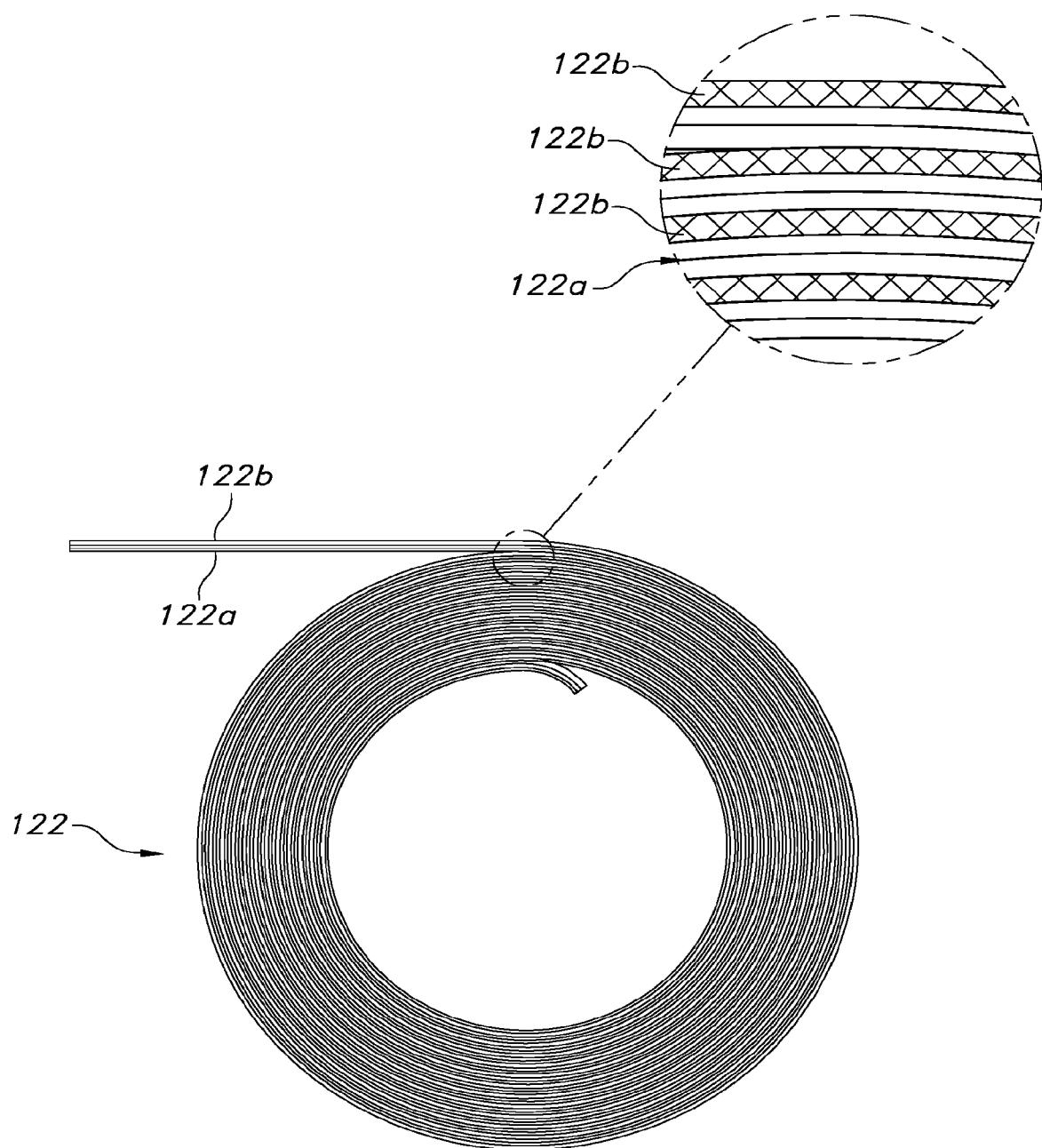
FIGS. 3A, 3B and 3C illustrate a matrix material for use in forming a structured fixed bed for culturing cells in any of the disclosed bioreactors.
Figure 3B:
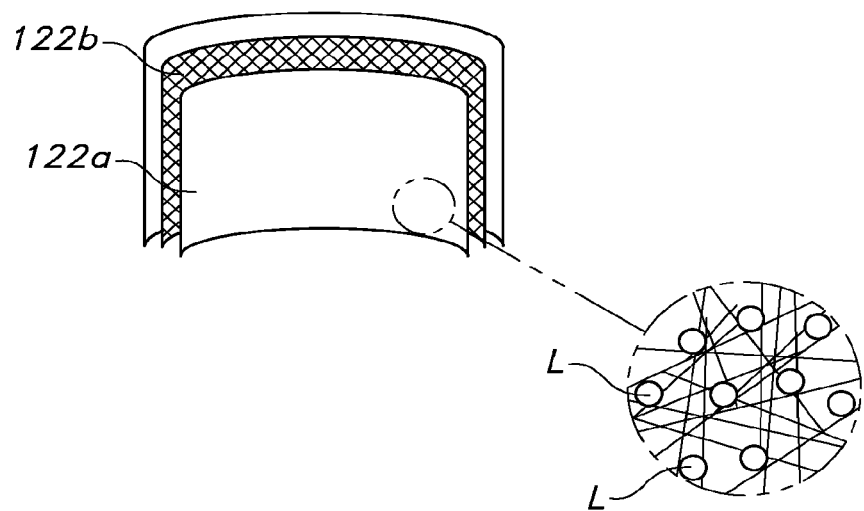
Figure 3C:
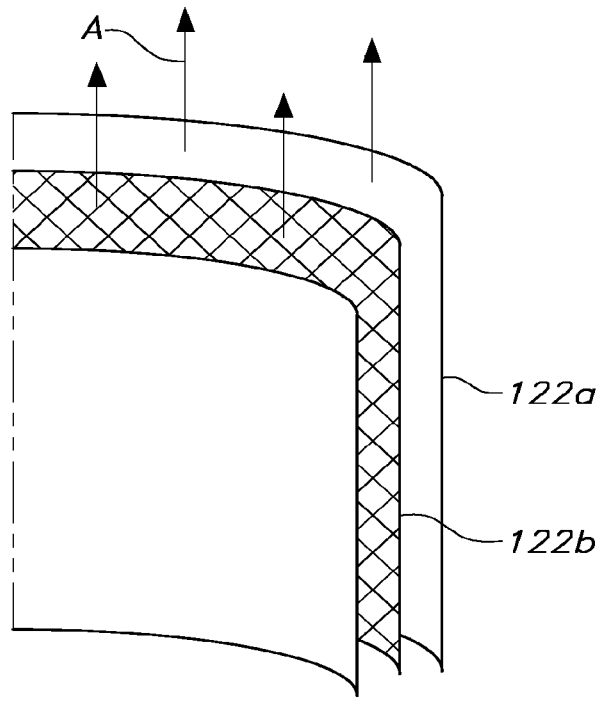

FIG. 3A shows one embodiment of a matrix material for use as a structured fixed bed in the bioreactor of the present disclosure and, in particular, a spiral bed 122. In some embodiments, one or more cell immobilization layers 122a are provided adjacent to one or more spacer layers 122b made from a mesh structure. In some embodiments, the layering may optionally be repeated several times to achieve a stacked or layered configuration. In some embodiments, the mesh structure included in spacer layers 122b forms a tortuous path for cells (see cells L in FIG. 3B suspended or entrapped in the material of the immobilization layer 122a), and a cell culture may form part of any invention claimed herein) and fluid to flow when layered between two immobilization layers 122a. Homogeneity of the cells is maintained within the structured fixed bed as a result of this type of arrangement. In some embodiments, other spacer structures can be used which form such tortuous paths. In some embodiments, as shown in FIG. 3A, the structured fixed bed can be subsequently spirally or concentrically rolled along an axis or core (e.g., conduit 128, which may be provided in multiple component parts). In some embodiments, the layers of the structured fixed bed are firmly wound. In some embodiments, the diameter of the core, the length and/or amount of the layers will ultimately define the size of the assembly or matrix. In some embodiments, thickness of each of the layers 122a, 122b may be between 0.1 and 5 mm, 01 and 10 mm, or 0.001 and 15 mm.

Figure 4:
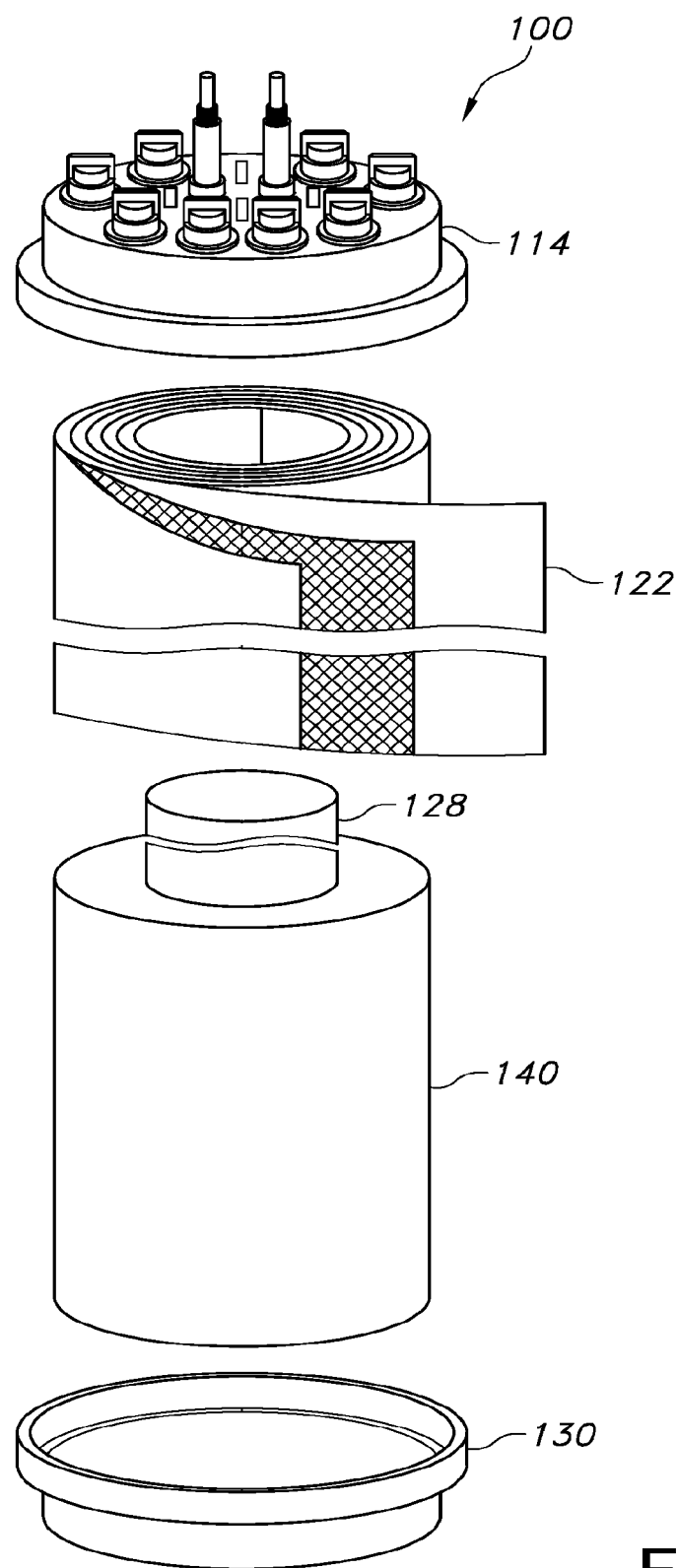
FIG. 4 illustrates a modular version of the bioreactor of FIG. 1.

According to one aspect of this disclosure, the bioreactor 100 in certain embodiments may be "modular." In some embodiments, a modular bioreactor can be comprised of a plurality of discrete modules that interact together to create a space suitable for culturing cells in a manner that is highly predictive due to the manufacturing homogeneity of the modules. In some embodiments, a modular bioreactor is not limited to particular shape or form (e.g., cylindrical or otherwise, and with a structured fixed bed or unstructured bed, depending on the application). For example, as shown in FIG. 4, In some embodiments, the modules may comprise a base portion formed by base module 130, an intermediate portion formed by an intermediate module 140 (which may be formed from a number of stackable modular portions, as outlined further in the description that follows), an optional associated central module, such as conduit or tube 128, which may also be considered part of the intermediate module, and a cover module, such as formed by a cover part in the form of lid or removable cover 114. In some embodiments, the modules may be separately manufactured as individual components and either assembled at a manufacturing facility based on an intended application (and then shipped to a point of use) or assembled based on an intended application at the point of end use. In some embodiments, the modules of the bioreactor 100 interact to create a place for growing cells, such as in a high-density manner using a fixed bed, such as for example a structured or unstructured fixed bed.

Figure 5:
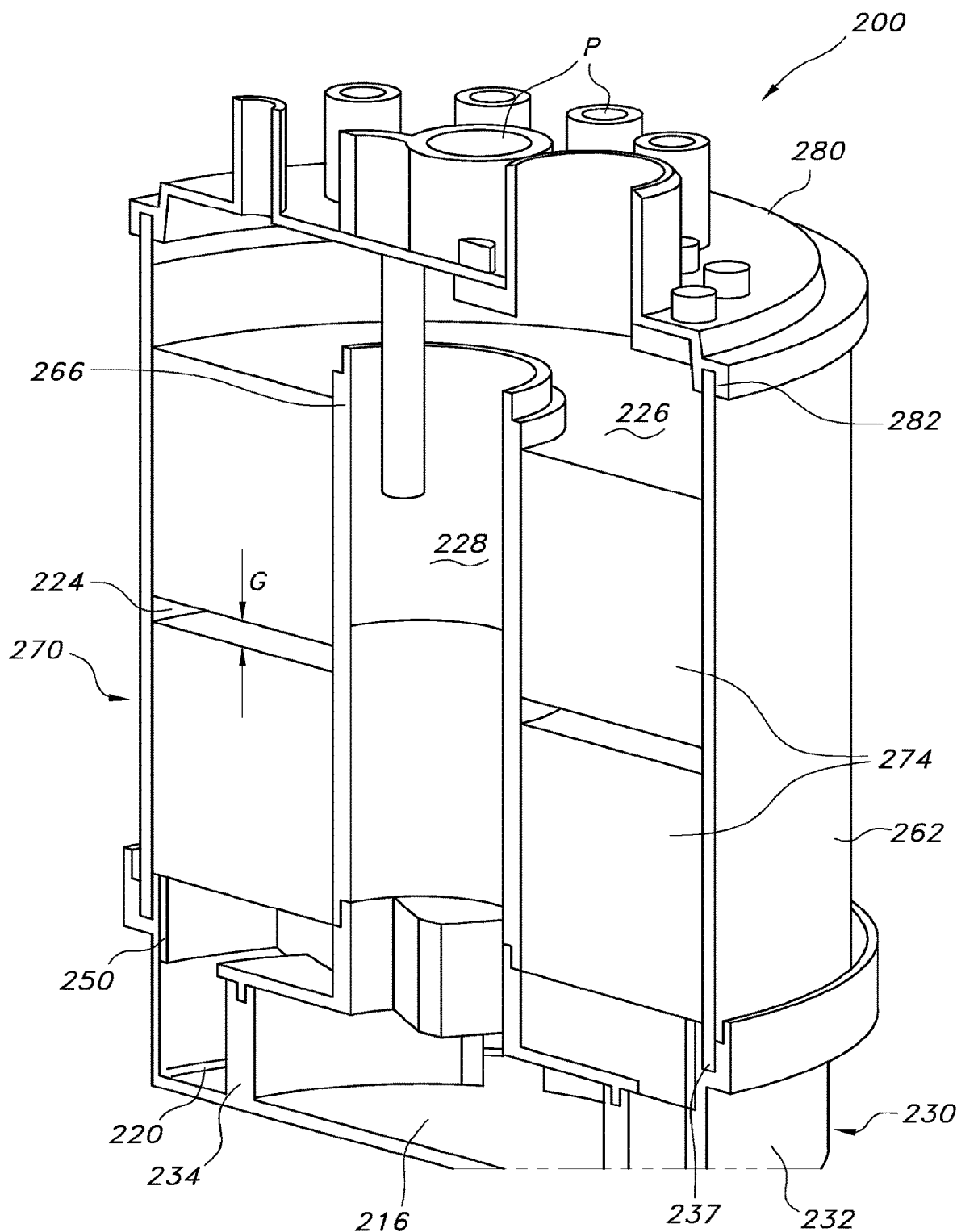
FIG. 5 is a cross-sectional view of a second embodiment of a bioreactor according to the disclosure.
Figure 6:
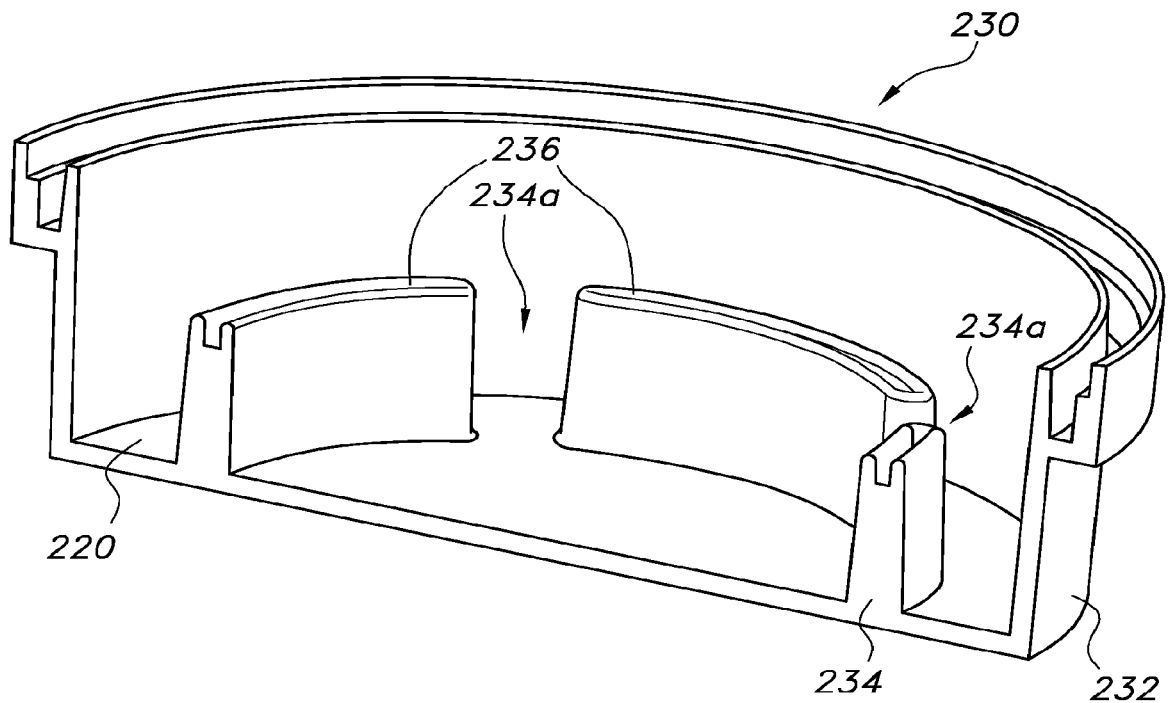
FIG. 6 is a cross-sectional view of a base portion of the bioreactor of FIG. 5.
Figure 7:
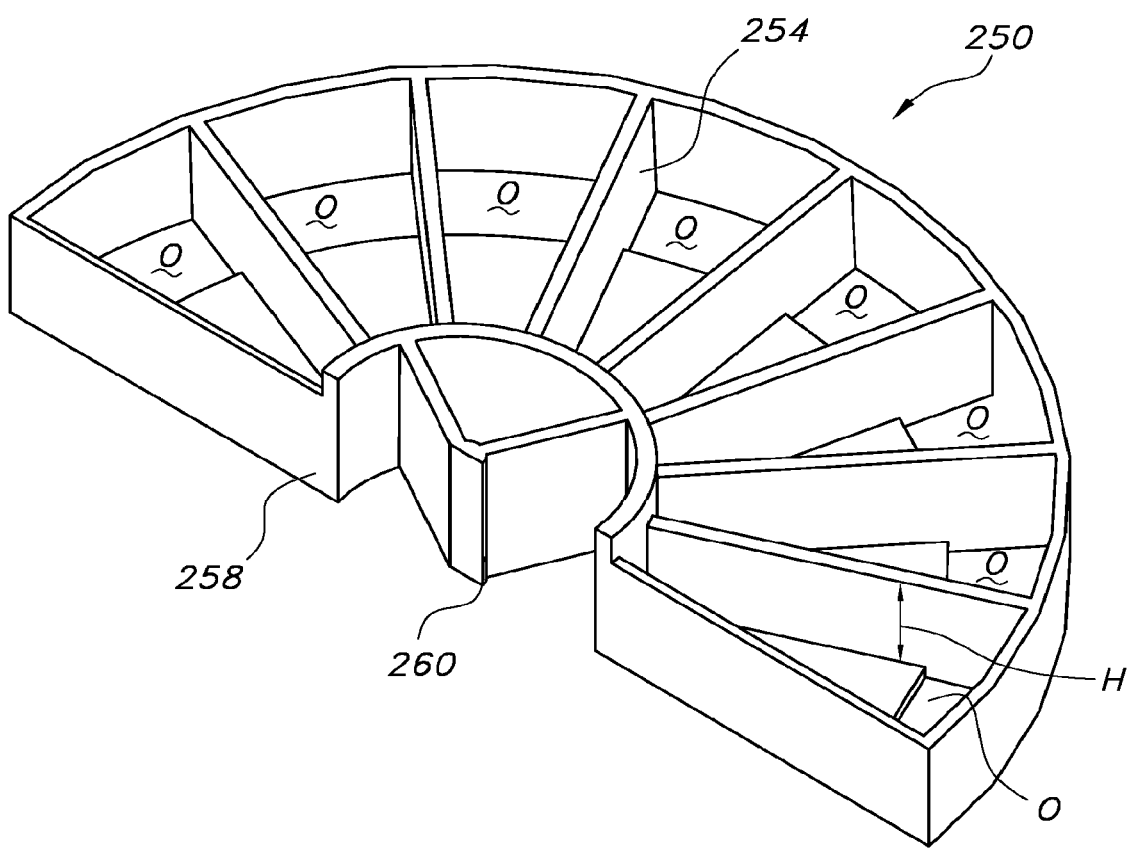
FIG. 7 is a partially cutaway top view of an intermediate part of the bioreactor of FIG. 5.

A further embodiment of a bioreactor 200 according to the disclosure is shown in FIGS. 5-9. In some embodiments, the bioreactor (whether modular or otherwise pre-assembled as a single unit) can comprise a base, an intermediate portion and a cover. In some embodiments, a base portion can comprise a base part 230. In some embodiments, an intermediate portion can comprise intermediate parts 250 and/or 270. In some embodiments, intermediate parts 250 and 270 are not identical. In some embodiments, a cover portion can comprise a cover part 280. Referring to FIG. 6, in some embodiments, base part 230 may include an external wall 232 and an internal wall 234, which may define a first chamber 216 for receiving the agitator (not shown). In some embodiments, the internal wall 234 can include openings 234a for allowing fluid flow to the second, radially outward chamber 220 bounded by the external or outer wall 232.

Figure 8:
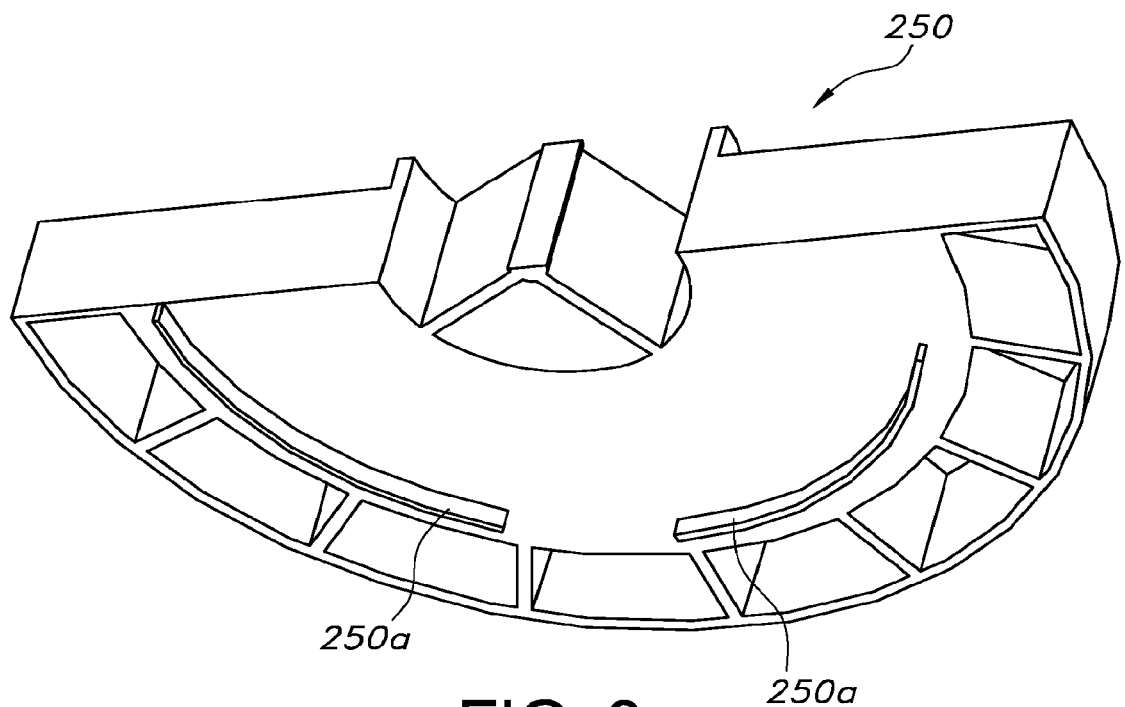
FIG. 8 is a partially cutaway bottom view of an intermediate part of the bioreactor of FIG. 5.
Figure 9:
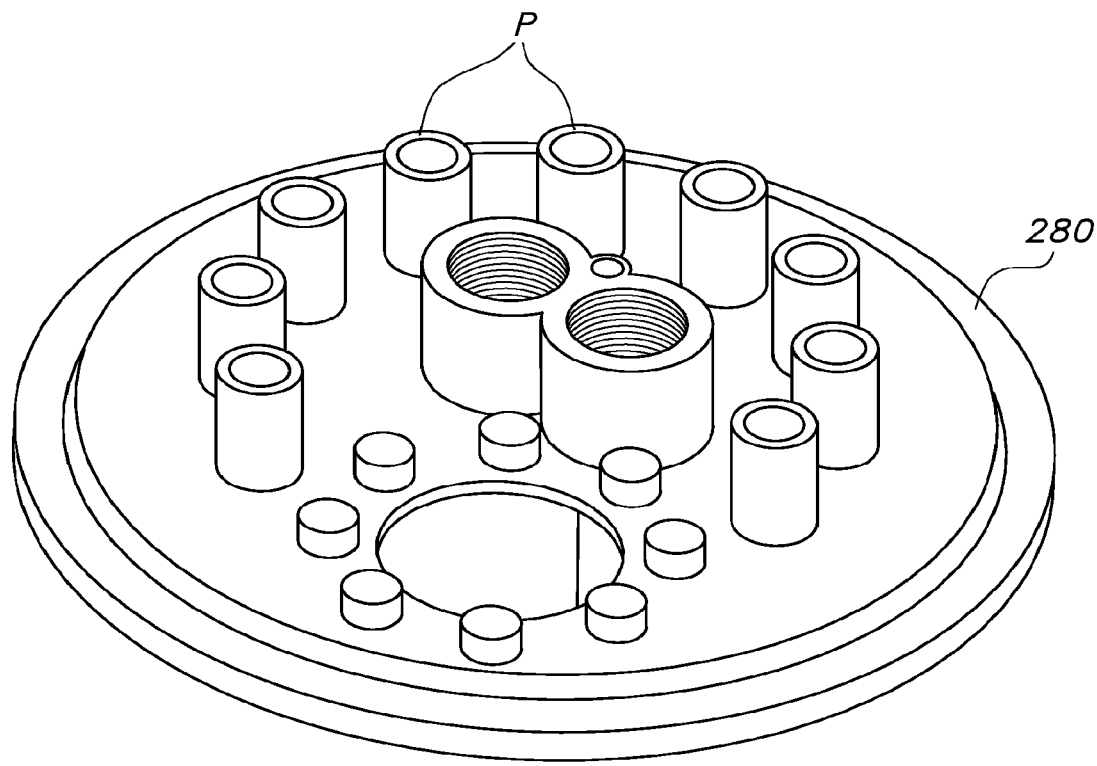
FIG. 9 is a perspective view of a cover portion of the bioreactor of FIG. 5.

As can be seen in FIG. 6, in some embodiments, the internal wall 234 may include a plurality of connectors, such as grooves 236, for engaging corresponding connectors, such as tongues 250a, on the first intermediate part 250, as shown in FIG. 8. In some embodiments, the internal wall 234 may be of lower/higher height than the external wall 232. In some embodiments, the internal wall 234 may be of lower height than the external wall 232, as can be seen in FIG. 8. With reference to FIG. 5, in some embodiments, the first intermediate part 250 may be at least partially recessed within the base part 230.

In some embodiments, the base part 230 may include a peripheral connector, such as a groove 237. In some embodiments, the connector or groove 237 can be adapted to receive a corresponding connector of a second intermediate part 270, which may simply be part of an outer wall 262 thereof. In some embodiments, within the intermediate part 270 can be located a plurality of fixed beds 274 in a third chamber 224 (but a single monolithic fixed bed could be used, which in this or any disclosed embodiment may take any size, shape, or form), which could be supported by an interposed support, but a gap G could also be provided between adjacent sections of fixed beds). The gap could also be eliminated, such that an upper bed rests on and is supported by a lower one.

In some embodiments, the structured fixed bed can be of the spiral form, as shown in FIGS. 3, 3A, 3B, and 3C (which spiral form can be implemented in any embodiment of a bioreactor, disclosed or otherwise). In the case of a spiral bed, the bed may be wound around an internal wall 266, which may form a fifth chamber 228 for returning fluid to the first chamber 216 in the base part 230. The internal wall 266 may comprise multiple stacked tubular parts, as shown. In some embodiments, the multiple stacked tubular parts can allow for the height to be adjusted depending on the number of fixed beds present (e.g., one tubular part may be provided for each stacked bed).

In some embodiments, the cover part 280, or lid can be adapted to removably connect with the second intermediate part 270, and thus form a fourth chamber 226 in which the liquid encounters gas, for example air. In some embodiments, the connection between the cover part and the second intermediate can be by a connector, such as a groove 282, which receives the upper end of the outer wall 262 or any access mechanism disclosed herein. The lid or cover part 280 may include various ports P.

Turning back to FIGS. 7 and 8, further details of the intermediate part 250 are shown. In some embodiments, part 250 may include a plurality of radially extending supports 254, which thus lend support for a structured fixed bed when resting thereon in the adjacent third chamber 224. In some embodiments, supports 254 may also support a lower shelf 256 defining a partial opening O for allowing fluid to flow vertically. In some embodiments, the height H of the supports 254 can be sufficient to allow the fluid to develop sufficient upward velocity before entering the chamber 224 to pass through the full section of the fixed bed 274.

In some embodiments, an inner annular wall 258 can be connected to the inboard end of the supports 254. In some embodiments, the wall 258, corresponds in diameter to the diameter of the internal wall 266 of the intermediate part 270, which may also connect with it (such as by nesting). In some embodiments, the internal wall 266 can form a passage for delivering fluid from the fifth chamber 228 to the first chamber 216. In some embodiments, a flow disruptor 260 may be provided in this passage to help prevent the creation of any vortex within the fifth chamber 228.

Figure 10:
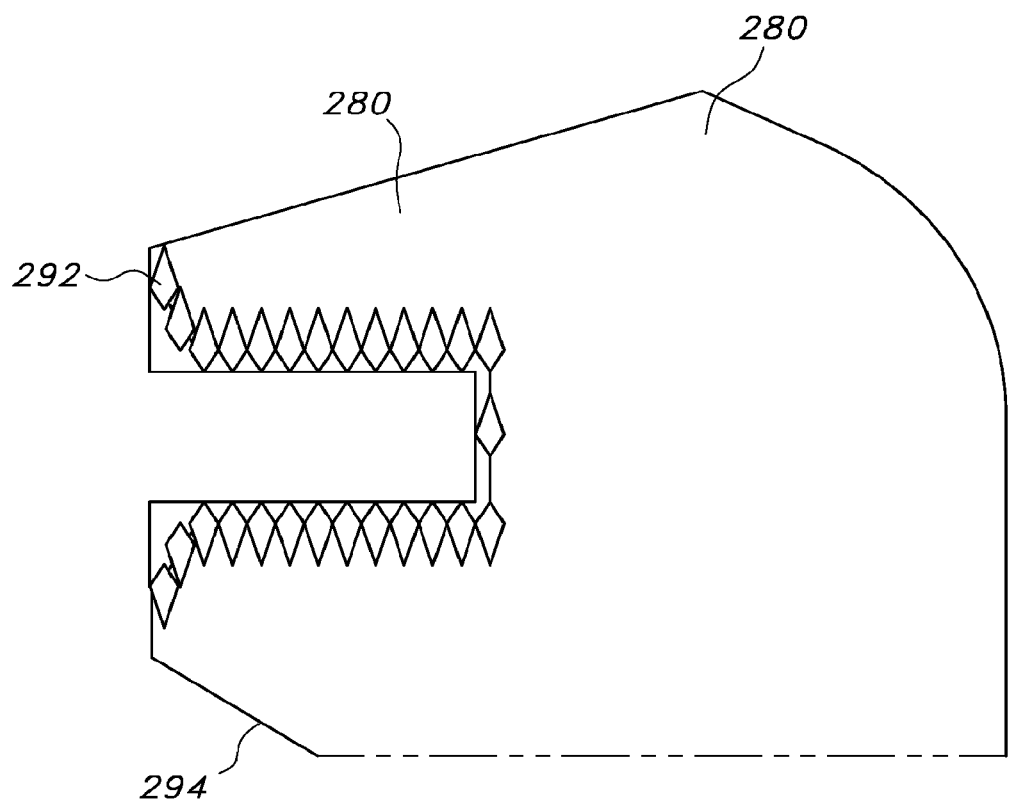
FIG. 10 is a cross-sectional view of a manner of providing metal threads in a plastic port.

In some embodiments, it may be desirable to provide one or more of the ports P on the cover part 280 with internal threading in order to establish a threaded connection with a component, such as a sensor (not shown). Thus, according to a further aspect of the disclosure, and with reference to FIGS. 9 and 10, the cover part 280 may be formed by providing a metal insert 292 with a helical thread into an injection mold 294, and then injecting a plastic material into the mold to form a composite part. In some embodiments, the threads may be reliably provided in the cover part 280, which may otherwise be formed of plastic. As can be appreciated, this technique may also be used in connection with any other parts of the disclosed bioreactors requiring threaded fittings or ports. In some embodiments, inserts for use in this technique may be obtained from Wilhelm Böllhoff GmbH & Co. KG of Bielefeld, Germany, under the IMTEC brand.

From FIG. 5, in some embodiments, it can be understood that the flow from one fixed bed module to the next-adjacent fixed bed module in the cell culturing chamber 224 can be direct or uninterrupted. In some embodiments, the outer chamber 224 can create a continuous flow path through the multiple beds located therein, which may be structured fixed beds, unstructured fixed beds, or unstructured beds. In some embodiments, the continuous and substantially unimpeded flow through the predesigned and matching bed modules helps to promote homogeneity for cell growth and other processing and enhances the consistency of the cell culturing operation, and also promotes the ability to take measurements or samples from the stacked beds, which is not readily possible if blocking partitions (as contrasted with the perforated supports, as discussed below) are present. Finally, in a structured bed embodiment, the manufacture of the overall bioreactor is even less complicated and labor intensive as the effort to match the properties and characteristics from one fixed bed module to the other is greatly reduced.

Figure 11:
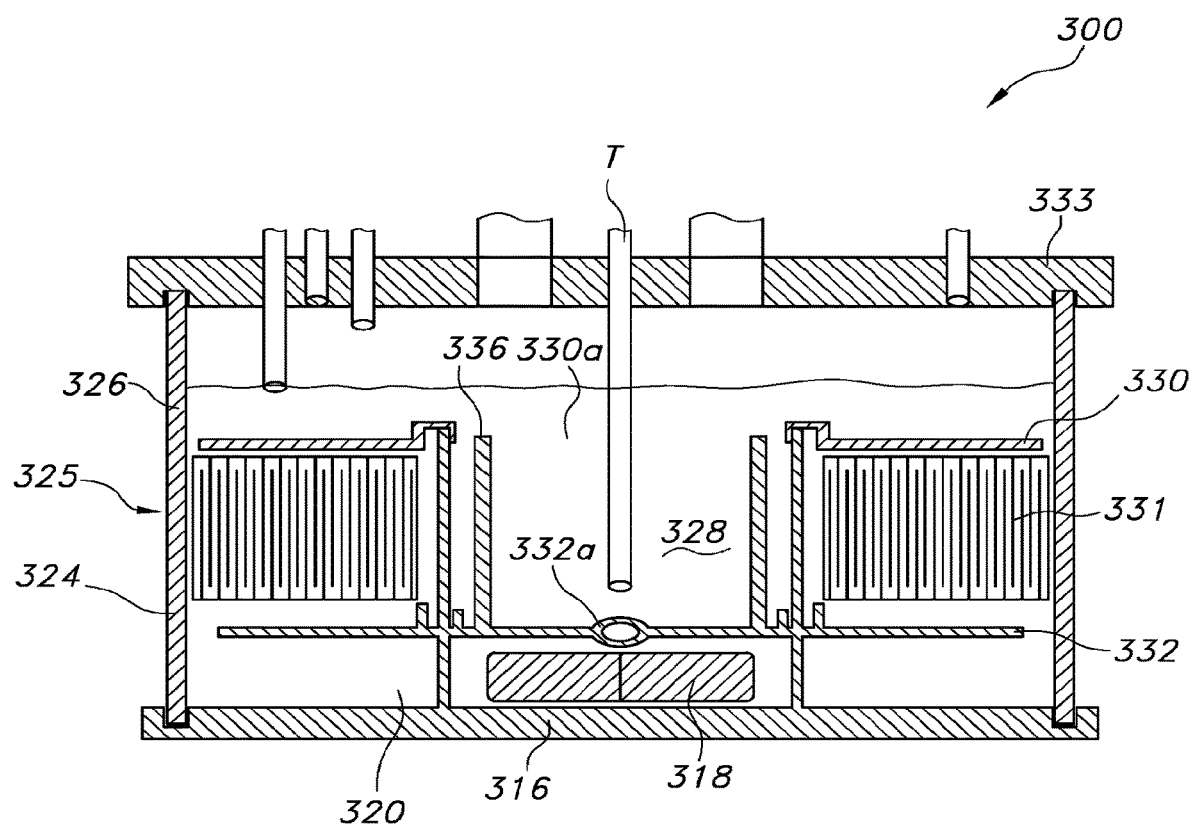
FIGS. 11, 11A and 11B are various view of a third embodiment of a bioreactor according to the disclosure.
Figure 11A:
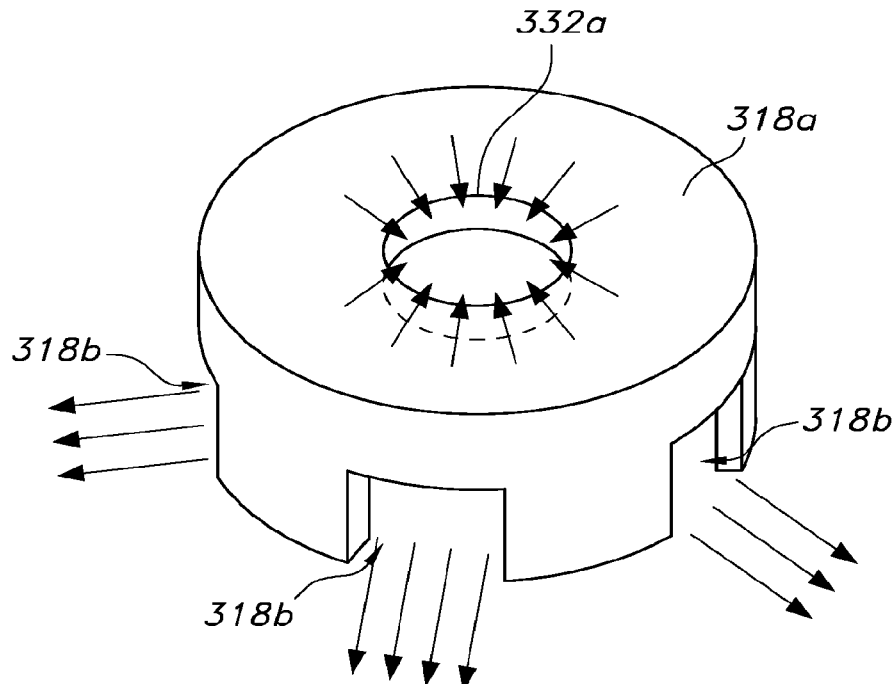
Figure 12:
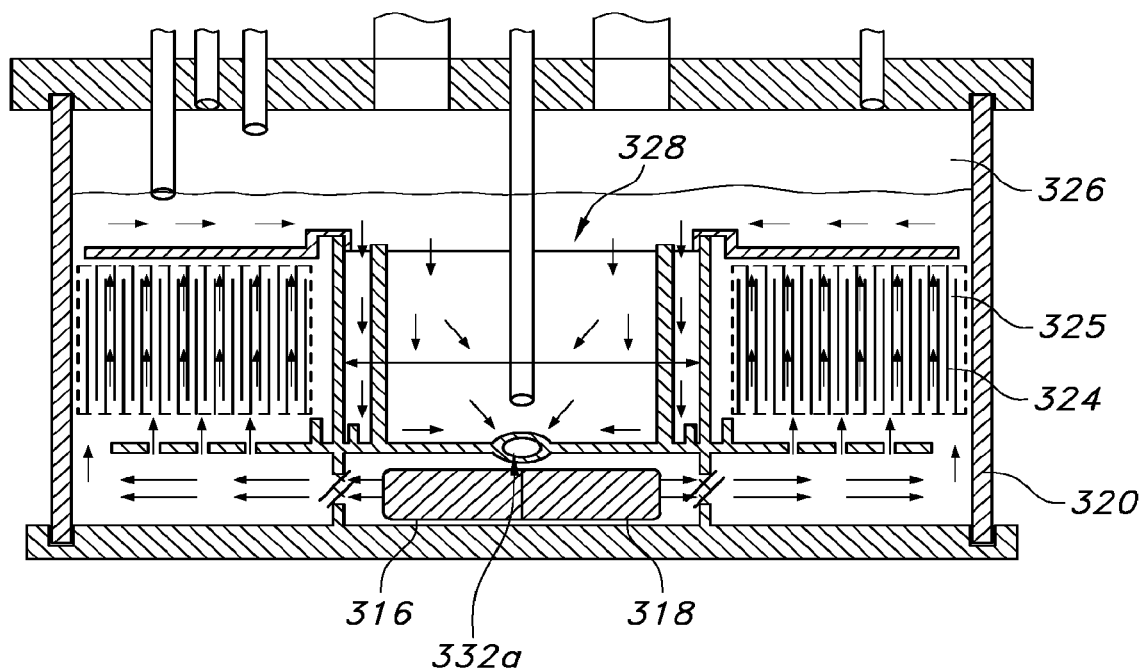
FIG. 12 is a cross-sectional view of the bioreactor of FIG. 11.

Reference is now made to FIGS. 11 and 12, which schematically illustrate a third embodiment of a bioreactor 300, which for purposes of clarity is shown in cross-section. In some embodiments, the bioreactor 300 (whether modular or otherwise pre-assembled as a single unit) comprises an external housing 331 with a cover 333, either of which may include various openings or ports for allowing for fluid introduction or removal. In some embodiments, within the bioreactor housing 331, several compartments or chambers are provided, including a first chamber 316 including an agitator for causing fluid flow within the bioreactor 300, which may be in the form of a "drop-in" rotatable, non-contact magnetic impeller 318 or an agitator disclosed herein. As indicated in FIG. 11A, in some embodiments, the impeller 318 may be housed, captured or contained within a housing, such as a housing or container 318a including a plurality of openings 318b serving as inlets and outlets for admitting and releasing fluid (but any other form of agitator could be used). In some embodiments, the agitation created may be such that fluid is caused to flow into a second or outboard annular chamber 320, which is radially outward of the first chamber 316.

In some embodiments, fluid may then flow upwardly (as indicated by arrows in FIG. 12) into a third annular chamber 324 along an intermediate, outer portion of the bioreactor 300. In some embodiments, the outer portion can be adapted to receive a fixed bed, such as a structured spiral bed 325, but other forms may be used), which in use may contain cells being grown. In some embodiments, the spiral bed 325 may be in the form of a cartridge that may simply be dropped into the chamber 324 at the point of use, or could be pre-installed in the chamber during manufacture at a facility prior to shipping.

In some embodiments, fluid exiting the third chamber 324 can then passed to a fourth chamber 326, where it is exposed to a gas (such as air) and then flows radially inwardly to a fifth chamber 328, which is columnar in nature and returns the fluid to the first chamber 316 for recirculation through the bioreactor 310, such that a continuous loop results. In some embodiments, a temperature probe or sensor T, or any other sensor disclosed herein may also be provided for sensing a parameter, for example the temperature of the fluid directly in the fifth chamber, and additional sensors (such as, for example, pH or dissolved oxygen) may also be provided at this location (which is before the fluid enters (or re-enters) the fixed bed 325).

Figure 11B:
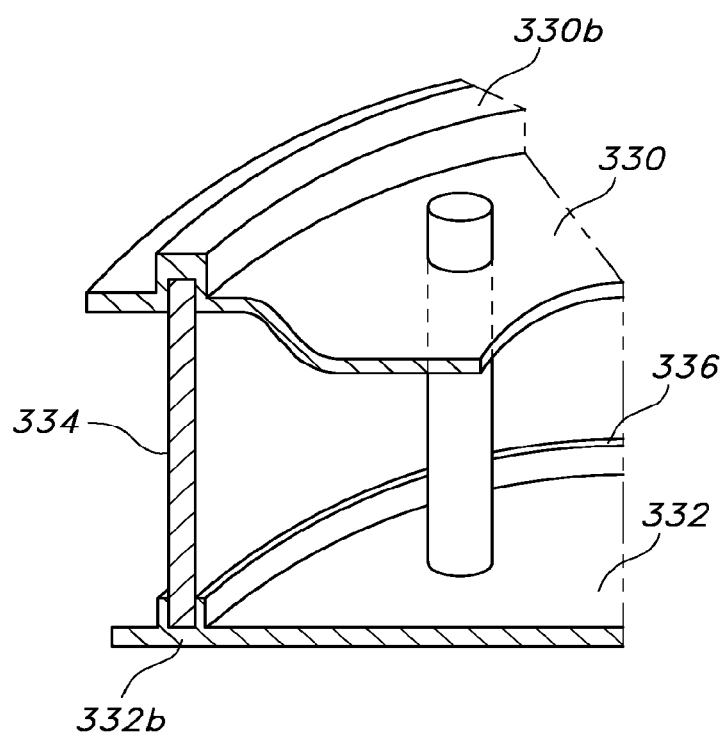

From the partially cutaway image at FIG. 11B, it can be understood that the third chamber 324 may be bounded by upper and lower plates 330, 332, which include openings or perforations for allowing fluid generally free of cells to enter and exit the fixed bed 325. In some embodiments, the lower plate 332 may include a central opening 332a for allowing fluid to pass from the fifth chamber 328 to the first chamber 316 for recirculation. In some embodiments, the upper plate 330 can include an opening 330a, into which fluid may travel to enter the fifth or return chamber 328.

In some embodiments, support for the upper plate 330 may be provided by a hollow, generally cylindrical tube 334, but could take other shapes. In some embodiments, the opposed ends of this tube 334 may fit into corresponding grooves 330b, 332b in the plates 330, 332 (in some cases the lower plate 332 can be integral with the impeller housing or container 318a in the illustrated embodiment). In some embodiments, supports, such as generally vertical rods 336, can be arranged to provide added support for the plate 330. In some embodiments, the disclosed vertical rods 336 do not interfere in any significant way with the fluid flow in the corresponding chamber 328. In some embodiments, the ends of the rods 336 may be recessed in the plates 330, 332, or held in place by suitable fasteners or locking mechanisms (e.g., locking connections, bolts or adhesives).

From FIG. 12 and the action arrows provided thereon, it can be understood that, as a result of the fluid agitation, in some embodiments, fluid may flow from the chamber 316 outwardly into chamber 320. In some embodiments, the fluid can then be redirected to pass vertically through chamber 324 including the fixed bed, and into chamber 328. In some embodiments, fluid is then directed inwardly to chamber 328, where the fluid may return to the first chamber 316 via opening 332a. In some embodiments, fluid can refer to culture medium.

Figure 13:
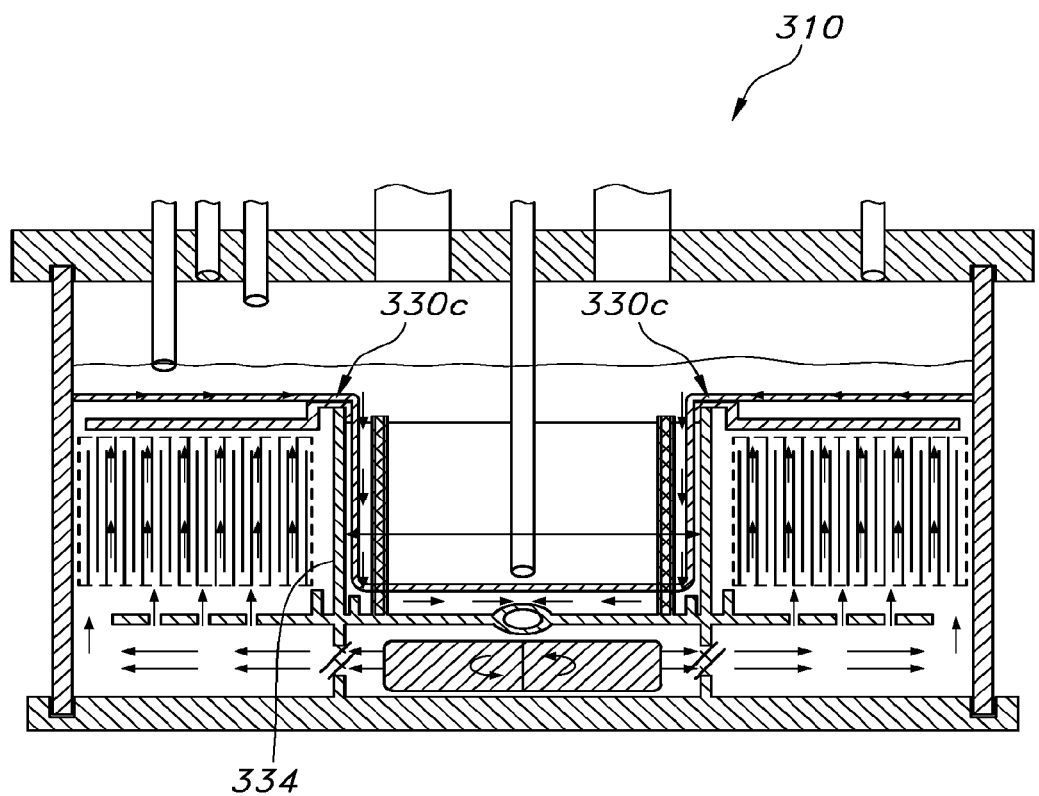
FIG. 13 is cross-sectional view of the bioreactor of FIG. 11.

FIG. 13 further illustrates an arrangement in which, in some embodiments, the upper plate 330 is provided with peripheral openings 330c to allow fluid to flow directly along the inner wall formed by tube 334. In this manner, a thin layer or film of fluid may be created, which flows downwardly while passing through the fifth chamber 328. In some embodiments, this may serve to increase the volume of the fluid exposed to gas (air) within the fifth chamber 328, prior to it being returned to the first chamber 316. In some embodiments, this implementation can allow for more oxygen transfer which may be needed for larger sizes or otherwise to increase cell growth rates adjust process parameters based on the biologic being produced.

In some embodiments, the "waterfall" implementation that creates a fluid film can be achieved by adding a limited quantity of cell culture medium from the start, such that only a small overflow results. Alternatively, in some embodiments, the "waterfall" implementation is achieved by adding cell culture medium and cells and then when cells are growing in the bed, withdraw culture medium (such as using a dip tube) in the corresponding chamber, such as chamber 328.

Figure 15:
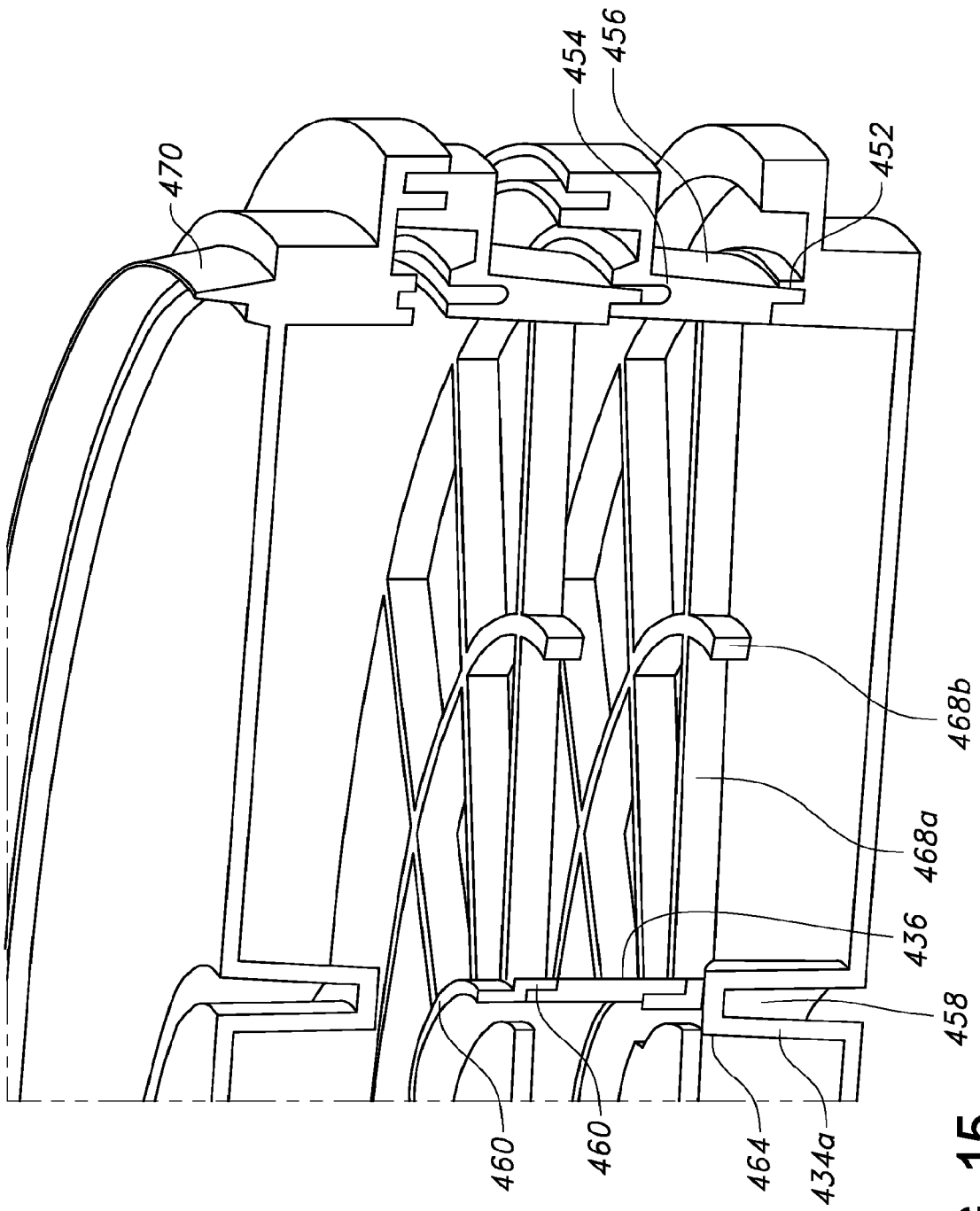
FIG. 15 is a partially cutaway view of a portion of the bioreactor of FIG. 14.

In some embodiments, a fourth embodiment of a bioreactor 400 is described with reference to FIGS. 14-16. In this embodiment, the bioreactor 400 includes the first through fifth chambers 416, 420, 424, 426, and 428 as noted above (fixed bed not shown), but the housing 412 is comprised of a plurality of modular parts. In some embodiments, the parts include a base part 430, one or more intermediate parts 450, and a cover part 470. In some embodiments, the parts 430, 450, 470 can be adapted to interact in a fluid-tight manner so as to form the bioreactor 400 with the chambers 416, 420, 424, 426, and 428, as noted.

In some embodiments, and as perhaps best understood from FIG. 14, the base part 430 can include a peripheral connector, shown in the form of a groove 432, for receiving and engaging a corresponding peripheral connector, such as a tongue 452, projecting from one of the intermediate parts 450. In some embodiments, interiorly, the base part 430 can include an upstanding wall 434, which defines the first chamber 416 for receiving a fluid agitator (not shown). In some embodiments, the wall 434 can includes openings or passages to allow for fluid to flow radially into an outer portion of the base part 430, which defines a further or second chamber 420. In some embodiments, as the flow is redirected vertically as a result of the presence of the base part 430, turbulence is created, which thus promotes mixing and homogeneity of the fluid throughout the bioreactor and thus enhances the cell culturing process.

Two intermediate parts 450a, 450b are shown as being stacked, with a peripheral connector (groove 454) of the first (lower) part 450a engaging a corresponding connector (tongue 452) of the second (upper) part 450b. As can be appreciated from FIG. 14, in some embodiments, each intermediate part 450a, 450b can include an outer side wall 456 supporting the tongue 452 and groove 454, respectively. In some embodiments, radially inwardly, an inner wall 458 carries inner and outer connectors, which may be in the form of upstanding ledges 460, 462, can be provided for receiving the corresponding ends of a tube 436, which thus forms periphery of the fifth or return chamber 428.

In some embodiments, the first or lower intermediate part 450a may also include openings, such as elongated arcuate slots 464, which at least partially receive connectors, of the base part 430, such as upstanding projections 434a from the wall 434. In some embodiments, an interior ledge 466 can form central openings 466a in the intermediate parts 450a, 450b for permitting fluid to flow in an inner column defined by the wall 434, as well as to receive any temperature sensor, dip tube or the like (which would be positioned after the fluid exits the fixed bed). In some embodiments, the second intermediate part 450b may be similarly constructed to promote interchangeability, in which case the openings (slots 464) in the second or upper intermediate part 450b allow for the creation of the thin falling flow or film of fluid within the fifth or return chamber 428, as previously noted.

In some embodiments, extending between the inner and outer walls 456, 458 are a plurality of supports 468. In some embodiments, the supports 468 include radially extending supports 468a and at least one circumferentially extending support 468b, which together can create a perforated or reticulated plate-like structure that allows fluid flow (which structure in this or any embodiment may comprise a screen, net, grid, or other skeletal structure, and may be rigid, semi-rigid, or flexible). In fact, the supports 468 may be designed to enhance fluid flow through the bed(s) by maximizing the amount of open space created by the openings for permitting fluid to pass. In some embodiments, for culturing cells, a fixed bed, such as the spiral bed (not shown) wound around wall 434 may be positioned in the chamber 424 formed between the parts 450a, 450b. In some embodiments, fluid passing from the upper intermediate part 450b can enters the fourth chamber 426 defined partially by cover part 470, and may flow to the column forming the fifth chamber 428 before returning to the first chamber 416 for recirculation.

In some embodiments, the cover part 470 includes a connector, such as tongue 472, for fitting into the corresponding connector (groove 454) of the second intermediate part 450b. In some embodiments, the cover part 470 can also include a first or central receiver, such as upstanding wall 474 for receiving a removable cap or lid 476, which may include various ports P for connecting with conduits for delivering fluids or other substances to the bioreactor 400 (and the fifth chamber 428). In some embodiments, the cap or lid 476 may also carry the temperature sensor or probe T, as shown, as well as other sensors, and may also be adapted for providing additions or removing substances from the bioreactor 400, or for regulating a product manufacturing process. As can be appreciated, in some embodiments, the cap or lid 476 can be well positioned to allow for sensing or fluid sampling to occur in connection with the return flow via chamber 428. In some embodiments, a second peripherally positioned receiver, such as upstanding wall 477, may also be adapted for connecting with a second cap or lid 478 for receiving sensors or depositing or withdrawing substances (including culture samples) from the bioreactor and, in particular, a peripheral portion thereof including the third chamber 426 in which cell culturing is completed. In some embodiments, the caps or lids 476, 478 may have different types of ports P and may be different sizes/shapes, or they may be identical to promote interchangeability.

By comparing FIG. 14 with FIG. 5, it can also be appreciated that the cap or lid 476, 478 may be used in connection with different sizes of bioreactors. Thus, in FIG. 14, it can be understood that the cap or lid 476, 478 has an outer diameter that is much less than an outer diameter of the bioreactor 400. In some embodiments, cap or lid 476, 478 could also be used with the bioreactor 300 of FIG. 5 (or any other), in which case the outer diameter would be about the same or perhaps even slightly greater than the diameter of the bioreactor 300.

In some embodiments, adhesives or glue may be used at the connections to hold the structures together. In some embodiments, threaded or locking (e.g., bayonet style) connections may also be used, such that a fluid-tight seal is maintained to prevent leakage and help ensure that sterility is maintained. In some embodiments, the arrangement of modular parts 430, 450, 470 allows for the bioreactor 400 to be pre-assembled, assembled or constructed on site rapidly, and potentially disassembled with similar rapidity. As it is possible to easily add additional tube(s) to form a heightened wall 434 or intermediate parts 450, the number of fixed beds or height of the bioreactor 400 may be adjusted to suit a particular need or process setting depending on the application.

In some embodiments, the flow from one fixed bed to the next-adjacent one in the chamber is direct or uninterrupted. In some embodiments, the outer chamber 424 for receiving the bed creates a continuous flow path through the multiple beds present therein, which may be structured fixed beds, unstructured fixed beds, or other beds. In some embodiments, the continuous and substantially unimpeded flow helps to promote homogeneity as if the modules are actually a single bed and thus improves the predictability and quality of the cell culturing process. Homogeneity means that the cell distribution throughout the bed is homogeneous or having a somewhat equal spread.

FIG. 16 illustrates an alternative embodiment of an intermediate part 450, which can be adapted for positioning above the base part 430. In some embodiments, a plurality of radially extending supports 466b are provided in the central opening 466a, which connect with an interior connector in the form of a ring 466d. In some embodiments, the ring 466d may be sized to receive part of a carrier 480 for carrying the agitator (not shown), and thus suspending it above the floor of the base part 430. In some embodiments, based on the structure, friction and concomitant particle shedding as a result of frictional contact between the impeller and the floor of the base part 430 during rotation is avoided.

As illustrated, in some embodiments, the carrier 480 may comprise a pair of compressible clips 482, which may be squeezed together to pass through opening in the ring 466d, and then released to securely suspend the carrier from the intermediate part 450, while permitting relative movement that allows the carrier to rotate freely. In some embodiments, the carrier 480 may include a socket 484, shown as being C-shaped in cross section, that receives a corresponding portion of the agitator, such as impeller (not shown) or perhaps simply an elongated magnetic or ferromagnetic rod (not shown). In some embodiments, this portion may comprise an upwardly extending projection rotatably connected to the agitator by a bearing. As can be appreciated, in some embodiments, the socket 484 can allow for side-to-side movement of the agitator, as may be necessary to achieve alignment with a corresponding external or non-contact (e.g., magnetic) drive D located external to the bioreactor 400, such as below the base part 430.

FIGS. 16A and 16B also illustrate an alternate embodiment of a modular bioreactor 400 including fixed beds 496. In some embodiments, the base part 430 and cover part 470 can be adapted for connecting with an outer casing 492, which creates a gap or space with the periphery of the intermediate parts 450. In some embodiments, the gap G or space may be used for providing a heating or cooling effect to control the temperature of the beds associated with the intermediate parts 450. The gap G or space may also simply supply insulation of the walls of the intermediate area of the bioreactor which are close to growing cells within the bed and likely to be sensitive to temperature variations. This insulation acts to prevent heat which is applied to the bottom of the base part 430 of the bioreactor from extending up to the adhered cells in the bed(s) 496.

FIG. 16A also illustrates the possible use of sparging in the bioreactor, which may be provided in any disclosed embodiment. In the illustrated arrangement, the sparging is provided by a sparger 494 located in the fifth chamber 428. The bubbles generated as a result may thus flow upwardly countercurrent to the return fluid flow.

These figures, and perhaps FIG. 16B best, also show that the intermediate parts 450 may engage internal tubes 436, which are fluid impervious to thus provide the chamber 428 for returning flow to the base part 430, where it may be agitated and returned to enter the beds from below and flow upwardly therethrough (in any embodiment disclosed). These tubes 436 may be provided such that one tube corresponds to each fixed bed 496 present, as shown, and two intermediate parts 450 engage each tube 436 (e.g., one from below and one from above). However, in this or any other disclosed embodiment, it should be appreciated that the innermost surface of the fixed bed, such as the innermost spiral wrap of a spiral bed, may be made to perform a similar function by making it or otherwise conditioning it so as to be impervious to fluid. For instance, the surface may be coated with a fluid-impervious or hydrophobic material, such that it still retains the fluid in the bed(s) and maintains a distinct, return flow of fluid through the central column formed by chamber 428.

FIG. 16C also illustrates an embodiment of the bioreactor 400 including the intermediate parts 450a, 450b sandwiching a fixed bed 496, which may be a structured, spiral bed as previously illustrated and described. The base part 430 and cover part 470 are also provided and interface with the outer casing 492, creating an annulus or gap, which again may be insulated or associated with a heating or cooling means. In this or any other embodiment, the casing 492 may simply create a buffer or space (filled with air or other gas). This may allow for the temperature of the bioreactor 400 to be regulated more efficiently (e.g., quicker) and further allows it to be perfused and/or used in media recirculation with a lower requirement in term of media pre-heating.

This figure also illustrates the housing 418 for an agitator 418a. The housing 418 may be any one of the forms shown in FIG. 21, and thus may include a flow divider 418d. The inner partition in the form of tube 436 for partially forming the central column (i.e., return chamber 428 shown in FIG. 16A) is also shown. An outer partition is also shown, may also be in the nature of a cylindrical structure or tube 496 that removably interconnects with the parts 450a, 450b (and may be adhered in place using adhesives or other forms of bonding), but could also be a unitary structure with one or both of them.

FIGS. 17 and 18 illustrate an example of a bioreactor 500 including one or more fixed beds, such as two vertically stacked, structured fixed beds 518a, 518b in the illustrated example. In some embodiments, the beds 518a, 518b can be arranged in an outer chamber 512a of the bioreactor 500 and may be the spiral beds shown in FIGS. 1-3. In some embodiments, an inner chamber 512b can also provide circulating fluid to or from the fixed bed(s). In some embodiments, the fluid may be caused to flow by an associated agitator, such as an impeller 520 located in a lower compartment 512c of the bioreactor 500. In some embodiments, the flow of fluids may be in a vertical direction within the fixed bed(s), such as from top to bottom or bottom to top. In some embodiments, the structured fixed bed(s) can be provided in the inner chamber 512b, with the outer chamber 512a serving to deliver fluid to and from the inner chamber.

Referring now to FIGS. 19 and 20, in some embodiments, an agitator in the form of an impeller 600 can be used in any of the above described embodiments is shown. In some embodiments, the impeller 600 may comprise magnets 602 that can be inserted into a body 604 (machined or injected) having radially extending blades 606, and an opening 608, and through which a shaft 610 or other receiver can be inserted. In some embodiments, caps (not shown) may be provided over the magnets 602 to ensure that contact is not made with the culture media, and may be attached using an adhesive or threaded connection. In some embodiments, the magnets 602 can be overmoulded when the body 604 embodiment will be injected (injection molded). In some embodiments, it may also be possible to 3D print the embodiment, to pause the 3D printing, to insert the magnets, and to relaunch the 3D printing to form the impeller 600. In some embodiments, the impeller body 604 may be made in a durable, polymer material, such as polycarbonate or other suitable materials. In some embodiments, the impeller can be machined, injection molded, 3D printed, or fabricated in or other ways. The associated receiver or shaft 610 (if present) may be formed of polypropylene or other suitable materials, and may be machined, injected or 3D printed.

FIG. 21 shows various combinations of impellers 600 with different containers 618a in a table form, with an indication of the relative efficiencies that result. In some embodiments, by adjusting the radial extent of the blades B and changing the number of outlets O in the container 618a to more than four (and possibly as many as 10-12), a higher efficiency in terms of fluid flow may be realized at a comparable rotational speed. In some embodiments, a divider, such as an upstanding wall 618d having an X-shaped cross-section may be provided adjacent to the inlet I of the container 618a for dividing the flow. In the two embodiments at the right of FIG. 19, it can also be understood that vanes V are providing for guiding the flow as it exits the container 618a and, as indicated, the vanes can have varying shapes or widths.

FIG. 22 further illustrates a further example of an impeller 650 having blades B that curve in a radial direction. In some embodiments, the impeller 650 may include a central space 651 for receiving flow from the inlet I of the container 618a when used in connection with such, and the blades B thus serve to redirect the fluid outwardly through the outlets O. The impeller 650 is shown as having 10 blades, but more or fewer may be provided as desired or necessary. In some embodiments, the impeller 650 may also include one or more magnets (not shown), as described above, for forming a non-contact coupling with an external drive (not shown). Because living cells are sensitive to mechanical forces such as shear, the impeller design needs to avoid shear while providing for efficient and optimized fluid flow. The impeller 650 achieves such complimentary goals.

Any of the components of the above bioreactors 100-500 may be made to be a single use or disposable component, or may be made to be reusable. Furthermore, the components used may be a mix or hybrid of disposable and reusable materials. In some embodiments, the bioreactor 100-500 may have a diameter of approximately 50-60 cm. In some embodiments, the bioreactor 100-500 may have a diameter or height of approximately more than about 5, 10, 15, 20, 25, 30, 35, 40, 45, 50, 60, 70, 80, 90 or 100 cm. In some embodiments, the cover part or lid 476, 478 that may be used in connection with bioreactor 400 may have a diameter of approximately more than 2, 4, 5, 6, 8, 10, 12, 15, 20, 25, 30 or 50 centimeters. In some embodiments, the intermediate parts 450a, 450b may have a height of approximately about 2.5-5.0 centimeters or more. In some embodiments, the overall bioreactor 400 may have a height of approximately 20-50 centimeters. In some embodiments, a bioreactor can comprise more than one fixed bed. In some embodiments, an impeller speed may be adjusted to compensate for an increase in pressure drop so as to maintain consistent linear velocity from bottom of reactor to top of reactor. In such case, shear stress on cells can be maintained constant for all sizes of bioreactor. In some embodiments, a sparger may also be provided. In some embodiments, it may be desirable during sparging to cease operation of the impeller to avoid transporting the air bubbles into the fixed bed.

In some embodiments, in the modular case, the bioreactor 100, 200, 300, 400, 500 may comprise any number of components for adjusting the relative height thereof. For example, a plurality of intermediate parts, such as parts 450, may be used to create an increased height. In some embodiments, the bioreactors 100, 200, 300, 400, 500 may also be provided in a number of different diameters, and each diameter may comprise one or more intermediate parts for creating different heights based on a particular application. In some embodiments, the fixed bed growth surfaces may range from <1 $m^2$ to 2 $m^2$, 7-30 $m^2$, 150-600 $m^2$, >2,400 $m^2$, and may vary among different sizes (height or diameter) of bioreactors. As noted, a plurality of fixed beds may be provided in a stacked configuration, such as one, two, three, four, or more fixed beds.

In some embodiments, in the above-described "waterfall" arrangements, it may be desirable to increase the oxygen transfer (or kLa, the volumetric mass-transfer coefficient that describes the efficiency with which oxygen can be delivered to a bioreactor for a given set of operating conditions) by providing a degree of turbulence as the fluid passes into the inner or central column. To achieve this result, one or more flow disruptors may be provided to interrupt the laminar flow and cause it to become turbulent. FIGS. 23 and 24 illustrate a further possible modification for the modular bioreactor, in which the flow disrupters or dividers may be provided as upstanding projections 702 on a ring 700 (thus forming a crown) which may be located above the central column. Consequently, fluid flow otherwise entering the central column 736 as a film may be "broken" by the projections 702, which thus form individual streams that are more turbulent and enable better oxygen transfer. In some embodiments, the projections 702 can break the potential swirling movement upon leaving the fixed bed, and ensure that the fluid flow can be aligned with the center of the bioreactor.

Turning to FIGS. 25 and 26, it can be understood that the resulting individual flows may ultimately recombine within the central column or columnar region formed by the inner wall of structured fixed bed, which may lead to added turbulence. Furthermore, it can be further understood that the ring 700 may cause the flow to assume a parabolic trajectory into the column, which can create a pocket P below the flow, where air/oxygen may become trapped. In some embodiments, to allow for gaseous exchange to occur between this pocket P and the interior of the bioreactor above the central column, one or more conduits 704 may be provided. In FIG. 25, a single conduit 704 is shown, which thus forms an inlet for gas flow. As shown in FIG. 25, multiple conduits 704a, 704b may be provided, and may serve as inlets and/or outlets for gas, such that it is renewed. As further indicated, the conduits 704 may be integral with the ring 700, as shown in FIG. 25, or may be separate from it, as shown in FIG. 26.

Turning now to FIGS. 27 and 28, a disposable (e.g., plastic or polymer) connector 800 for connecting a non-disposable (e.g., stainless steel) probe 802 for sensing various conditions of the bioreactor 100, 200, 300, 400, 500 is shown. In some embodiments, the connector 800 may comprise a tube or sleeve 804 associated with a cap or cover 806 at one end, and an adaptor 808 at the other, which may be for connecting with a port in any wall or portion of the bioreactor 100, 200, 300, 400, 500 such as by way of a threaded connection. In some embodiments, an optically transmissive portion, such as a membrane 810 attached to the cap 806, may be provided for interfacing with the probe 802.

EXAMPLES

The following examples are given for the purpose of illustrating various embodiments of the invention and are not meant to limit the present invention in any fashion. The present examples, along with the methods described herein are presently representative of exemplary embodiments, and are not intended as limitations on the scope of the invention. Changes therein and other uses which are encompassed within the spirit of the invention as defined by the scope of the claims will occur to those skilled in the art. The following example is provided to illustrate the efficacy of the disclosed bioreactor.

A bioreactor was prepared per FIG. 1 by hydrating a structured fixed bed under aerated and agitated conditions (750 mL culture medium ensuring a falling film of ~5 cm, 740 rpm (corresponding to a vertical linear velocity of 1 cm $s^{-1}$ through the fixed bed), 1 hour hydration time). Medium equilibration was achieved by setting the temperature and pH at the experimental set points (respectively 37° C., 7.2) and starting the automated regulations. DO calibration was first achieved under non-regulated, aerated conditions (100% DO set point), subsequently to which the DO regulations (>50%) was started. Probe calibration (on and offline measurements) was performed once the medium had reached the set operating temperature. Inoculum was manually transferred to the bioreactor at an initial seeding density of $3.0\times10^4$ cells $cm^{-2}$ under agitated conditions, ensuring that the total liquid volume remained constant by removing the corresponding volume of equilibration medium. Culture parameters recording (pH, DO, T) was started immediately thereafter. An external media source was connected and recirculated through the bioreactor shortly after inoculation, per FIG. 2.

Using this experimental set up, two cell cultures were performed for 3 days in batch mode (infection cell density=$1.9\pm0.2\times10^5$ cells $cm^{-2}$). A third cell culture was performed for 6 days (infection cell density=$6.5\times10^5$ cells $cm^{-2}$) with the replacement at day 3 of the external media source with fresh material to ensure nutrient availability. Infection was performed using an adenovirus (stock: $1.7\times10^9$ ifu $mL^{-1}$) at a set target cell density of infection and fixed MOI of 5. Harvest of the cell culture medium was performed using an optimized detergent addition (Triton™

X-100; Sigma Aldrich, Overijse, Belgium) for in-situ bulk cell lysis under agitated conditions. The following summary is provided:

Bioreactor vessel effective working volume: 750 mL
Recirculation volume: 4.2 L
Agitation speed: 740 rpm (1 cm s−1 vertical velocity)
Falling film height: ~5 cm
Innoculation density: 25,000-30,000 cells cm−2
pH: 72
Dissolved oxygen: 50%
Harvest treatment: Triton X-100, Benzonase and MgCl2−
Culture time: 3-6 days Control adherent cultures in a CELLSTACK bioreactor were performed under identical operating conditions where relevant (temperature, media composition, initial pH, headspace gas composition). FIG. 29 shows the cell growth curves in inventive fixed bed bioreactor compared to their controls carried out in CELLSTACK bioreactor. The cell density reached in the structured fixed bed bioreactor is higher under the same conditions than in the control experiment, both at day 3 and even more so at day 6 ($6.5 \times 10^5$ vs. $3.2 \times 10^5$ cells cm−2). In order to achieve the high 10 cell density observed at day 6, 85% of the medium was exchanged at day 3 in the CELLSTACK bioreactor, while an external bottle containing 4.2 L of fresh culture medium was connected and circulated (10 mL min−1) through the bioreactor, corresponding to the same ratio of medium exchange. Infection was performed at a target cell density in the cell culture. All cells were observed to be lysed 3 days post infection, an observation upon which it was decided to recover the product using the detergent treatment. The same harvest protocol was performed on the control with the CELLSTACK bioreactor and the data is presented alongside the bioreactor runs in FIG. 30. Bioreactor #2 according to the disclosure was operated with an external medium circulation loop of 4.2 L from the onset and infected at day 3 (see Methods for further details—cell density post-infection not shown). Bioreactor #1 according to the disclosure was started just like bioreactor #2 except that at day 3 the external media circulation loop was replaced with fresh medium thus allowing further cell growth. Bioreactor #2 was infected at day 2 whereas bioreactor #3 was infected at day 3. The error bar represents the range of the TCID50 analytical assay measurement. The productivity between the inventive bioreactors and their control is similar and the differences are within the error range of the assay.

A further experiment was conducted to demonstrate the efficacy of a structured fixed bed in a bioreactor, as shown in FIGS. 31 and 32. The cell culture conditions were as follows:

Vero cells
Media 5% serum-volume/surface ratio: 0.17 ml/cm$^2$
Inoculation 5000c/cm$^2$
5 days of growth
37° C.-pH: 7.2-DO=50%
Agitation of the bioreactor: 550 rpm
Recirculated batch mode with a flow of 20 ml/min As can be appreciated, these figures illustrate that uniform cell growth was achieved, both axially and radially. with the bioreactor using a structured fixed bed, and in particular, a spiral or "snail" bed.

Figure 36:
Figure 37:
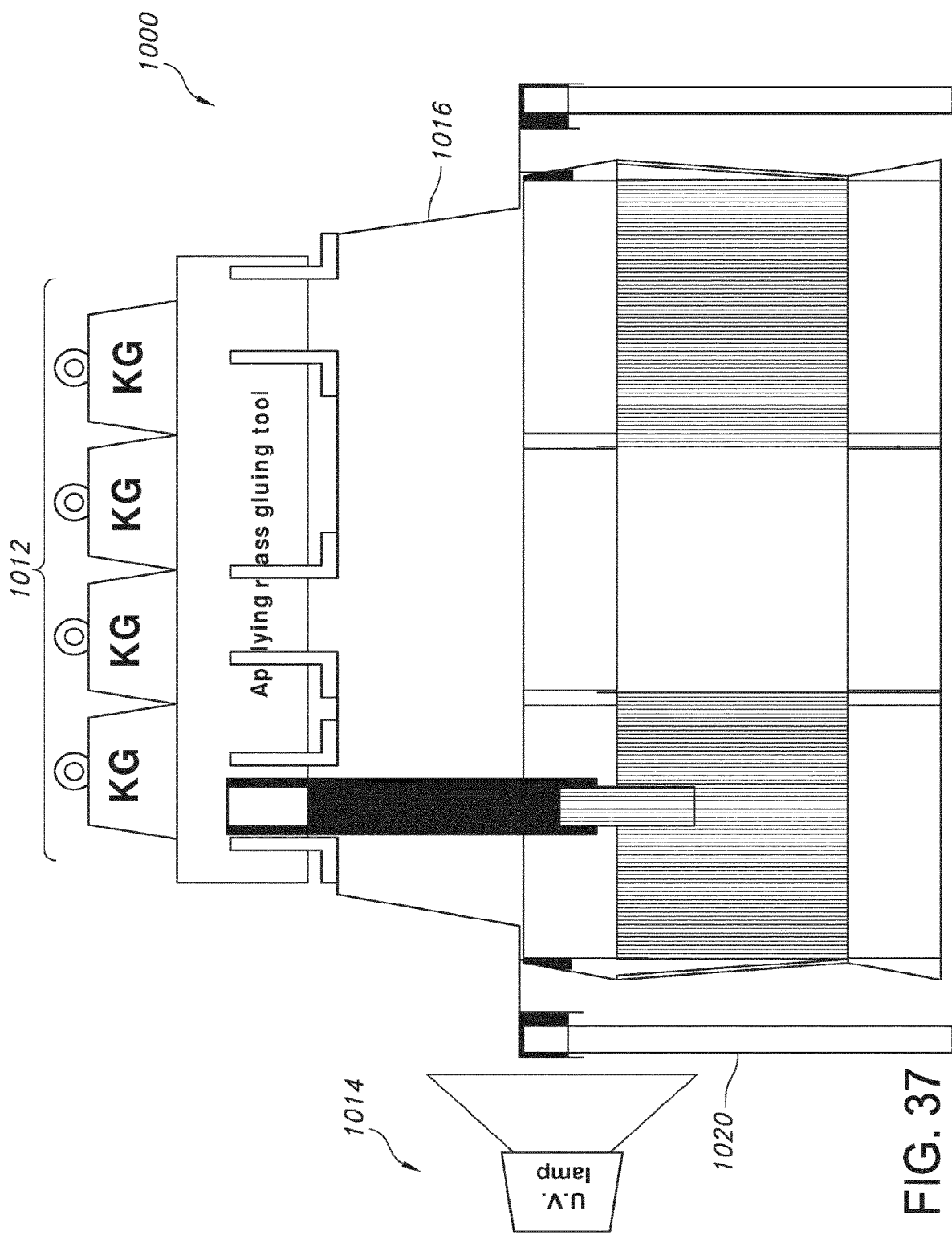

Referring now to FIGS. 33-37, a method of manufacturing a modular bioreactor 1000 having a structured fixed bed is disclosed. Turning first to FIG. 36, the method may comprise associating a tubular part 1002 with the structured fixed bed, which may be the spiral bed 1004 previously described. The spiral bed 1004 may be formed by wrapping or winding the matrix material around the tubular part 1002, which may be fastened to a base 1006, such as by using a tongue and groove arrangement, and adhered in place. This forms a first stage bioreactor precursor 1007.

Figure 38:
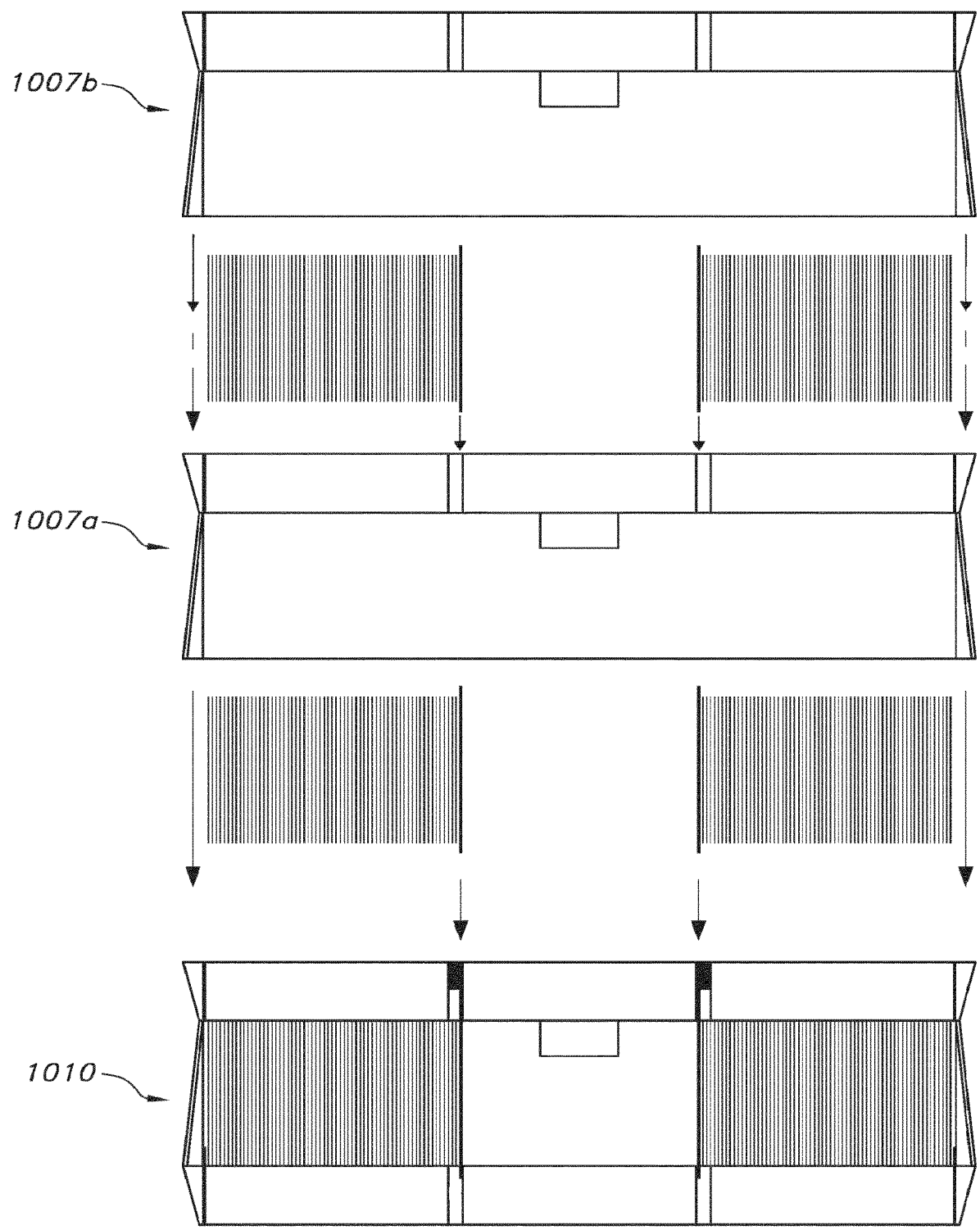

Next, an upper portion 1008 may be secured to the base 1006, also using an adhesive. This is done to arrive at a second stage bioreactor precursor 1010, as shown in FIG. 38, which further shows the use of weights 1012 for ensuring proper seating of the parts and a UV lamp 1014 for curing the adhesive.

With reference to FIG. 39, a lid 1016 may then be applied to the bioreactor precursor 1010, and any probe or sampler 1018 installed. The lid 1016 may interface with an outer housing 1020, which may be adhesively bonded together. Weights 1012 and the UV lamp 1014 may again be used to form a secure connection.

With reference to FIG. 41, it can be understood that prior to installing the lid 1016, a stacked configuration may be achieved by installing multiple first stage bioreactor precursors 1007a, 1007b onto a second stage bioreactor precursor 1010. The upper portion 1008 of the second stage bioreactor precursor 1010 may be adapted to receive a portion of the next adjacent first stage bioreactor precursor 1007a, such as a depending portion of the tubular part 1002. Likewise, the upper portion 1008 of the first stage bioreactor precursor 1007a may be adapted to interface similarly with the next adjacent second stage bioreactor precursor 1007b. Lid and any probes, samplers, or the like may be installed as noted above, and the bioreactor 1000 provided with multiple stacked beds in this manner.

A further method of manufacturing a bioreactor is also contemplated. In this method, structured fixed beds are placed into an interior compartment or chamber of the bioreactor. As noted previously in the disclosure, the beds may be in contact, or separated by a spacer (e.g., a screen or like structure) or a gap.

In any embodiment, it can be appreciated that the monolithic nature of the structured fixed beds in the bioreactors 100, 200, 300, 400, 500 help to promote consistency of the cell culturing operation throughout, and thus homogeneity. The ability to simply "drop in" a structured fixed bed into a bioreactor makes the cell culturing process easily repeatable, and the results subject to high reproducibility. This is a significant advantage over known bioreactors using suspended or fluidized beds. As a result of the disclosed arrangements, cell culture homogeneity (e.g., characteristics including temperature, pH and other reagent characteristics) is maintained throughout. Homogeneity is further improved due to the impeller mixing and fluid flow. Homogenization is further improved due to the gaps where re-homogenization (remixing) of the cell culture medium occurs. Even if cell culture travels through the bed and it loses homogeneity, that homogeneity is somewhat restored as the culture passes through the gaps.

Summarizing, this disclosure may also be considered to pertain to the following items:

1. An apparatus for culturing cells in connection with a fluid flow, comprising: a modular bioreactor including a fixed bed for culturing cells.
2. The apparatus of item 1, wherein the modular bioreactor comprises: a base portion having a first chamber, an intermediate portion forming at least part of a second, outer chamber for receiving the fixed bed and at least part of a third inner chamber for returning fluid flow from the second outer chamber to the first chamber, and a cover portion for positioning over the intermediate portion.
3. The apparatus of item 1 or 2, wherein the fixed bed comprises a structured fixed bed.
4. The apparatus of any of the foregoing items, wherein the intermediate portion comprises a tubular part, the structured fixed bed extending spirally around the tubular part.
5. The apparatus of any of the foregoing items, wherein the intermediate portion comprises a tubular part formed by an inner wall of the fixed bed.
6. The apparatus of any of the foregoing items, wherein the intermediate portion comprises a plurality of intermediate parts, each associated with a structured fixed bed.
7. The apparatus of any of the foregoing items, wherein at least one of the plurality of intermediate parts is perforated for allowing fluid to flow from a first structured fixed bed below the at least one intermediate part to a second structured fixed bed above the at least one intermediate part.
8. The apparatus of any of the foregoing items, wherein each of the plurality of intermediate parts is tubular, and each structured fixed bed comprises a spiral bed wound around the tubular intermediate part.
9. The apparatus of any of the foregoing items, further including a perforated support for the structured fixed bed.
10. The apparatus of any of the foregoing items, wherein the intermediate portion further includes a tubular casing for forming a periphery of the modular bioreactor, the tubular casing forming a space for heating, cooling, or insulating the bioreactor.
11. The apparatus of any of the foregoing items, wherein the intermediate portion comprises a plurality of intermediate parts, each adapted for connecting with each other.
12. The apparatus of any of the foregoing items, wherein the intermediate portion includes a tube for engaging at least one intermediate part and forming an inner wall of the outer second chamber for receiving the fixed bed.
13. The apparatus of any of the foregoing items, wherein the tube engages a first intermediate part below the tube and a second intermediate part above the tube.
14. The apparatus of any of the foregoing items, wherein the second intermediate part includes openings for creating a fluid film along the third inner chamber.
15. The apparatus of any of the foregoing items, further including supports for supporting the second intermediate part from the first intermediate part.
16. The apparatus of any of the foregoing items, wherein the supports comprise vertical rods.
17. The apparatus of any of the foregoing items, wherein the cover portion comprises a removable cap including a plurality of ports.
18. The apparatus of any of the foregoing items, wherein the removable cap has an outer diameter that is less than an outer diameter of the intermediate portion.
19. The apparatus of any of the foregoing items, wherein at least one of the ports includes a threaded metal insert.
20. The apparatus of any of the foregoing items, wherein the cover portion has an outer diameter that is equal to or greater than an outer diameter of the intermediate portion.
21. The apparatus of any of the foregoing items, wherein the intermediate portion comprises an intermediate part adapted for positioning at least partially within the base portion, the intermediate part further including a flow disruptor for disrupting fluid flow.
22. The apparatus of any of the foregoing items, wherein the base portion includes a further chamber radially outward of the first chamber in fluid communication with the second outer chamber including the fixed bed, which is formed by an upstanding wall having a plurality of openings for transmitting fluid from the first chamber to the further chamber.
23. The apparatus of any of the foregoing items, further including an agitator associated with the base portion.
24. The apparatus of any of the foregoing items, wherein the intermediate portion is adapted for suspending the agitator in the first chamber in a manner that allows side-to-side movement for alignment with an external drive.
25. The apparatus of any of the foregoing items, further including a container for containing the agitator, the container including a central inlet and a plurality of radially oriented outlets.
26. The apparatus of any of the foregoing items, wherein a flow divider is associated with the central inlet.
27. The apparatus of any of the foregoing items, wherein the agitator comprises a plurality of curved blades.
28. The apparatus of any of the foregoing items, further including a plurality of flow disruptors for dividing the fluid flow entering the third inner chamber into a plurality of streams.
29. The apparatus of any of the foregoing items, wherein the plurality of flow disruptors are associated with a ring.
30. The apparatus of any of the foregoing items, further including one or more conduits for permitting gas to enter into a space behind one of the streams.
31. The apparatus of any of the foregoing items, wherein the one or more conduits are connected to a structure including the plurality of flow disruptors.
32. The apparatus of any of the foregoing items, wherein a first conduit is connected to the structure.
33. The apparatus of any of the foregoing items, wherein first and second conduits are connected to the structure.
34. The apparatus of any of the foregoing items, wherein first and second conduits are not connected to the structure.
35. An apparatus for culturing cells, comprising: a modular bioreactor comprising a base portion connected to both a central column and an outer casing, the outer casing and central column together forming a compartment for culturing cells.
36. The apparatus of item 35, wherein the compartment includes at least one structured fixed bed.
37. The apparatus of item 35 or item 36, wherein the compartment includes a plurality of structured fixed beds, arranged in a stacked configuration.
38. The apparatus of any of items 35-37, further including an intermediate part between at least two of the plurality of structured fixed beds.
39. The apparatus of any of items 35-38, wherein the at least one structured fixed bed comprises a spiral bed.
40. The apparatus of any of items 35-39, wherein each of the plurality of stacked, structured fixed beds is wrapped around the central column.
41. The apparatus of any of items 35-40, wherein the central column comprises first and second interconnected tubes, a first structured fixed bed of the plurality of structured fixed beds being wrapped around the first tube and a second structured fixed bed of the plurality of structured fixed beds being wrapped around the second tube.
42. The apparatus of any of items 35-41, wherein the central column comprises first and second tubes for engaging a perforated support extending between at least two of the plurality of structured fixed beds.
43. The apparatus of any of the foregoing items, wherein the fixed bed comprises a cartridge adapted for being inserted into and removed from the second, outer chamber or compartment.
44. The apparatus of any of items 35-43, wherein the base portion is removably connected to the central column.
45. The apparatus of any of items 35-, wherein the base portion is removably connected to the outer casing.
46. A bioreactor for culturing cells, comprising:
    a base part having a first chamber including an agitator for agitating a fluid; and
    a first central column removably attached to the base part, the first central column forming at least part of a second, outer chamber for culturing cells and a third inner chamber for returning fluid flow from the second outer chamber to the first chamber.
47. The bioreactor of item 46, wherein the second, outer chamber includes a first structured fixed bed.
48. The bioreactor of item 47, wherein the first structured fixed bed comprises a spiral bed.
49. The bioreactor of item 48, wherein the first structured fixed bed is wound around the first central column.
50. The bioreactor of any of items 47-49, further including a second central column forming at least part of the second outer chamber, and further including a second structured fixed bed spaced vertically from the first structured fixed bed.
51. The bioreactor of item 50, further including a perforated support between the first structured fixed bed and the second structured fixed bed.
52. The bioreactor of item 46, wherein the second, outer chamber includes an unstructured bed.
53. A bioreactor for culturing cells in connection with a fluid, comprising:
    a first chamber including an agitator for agitating the fluid;
    a second, outer chamber including a plurality of stacked beds for culturing cells; and
    a third, inner chamber for returning fluid from the second outer chamber to the first chamber.
54. The bioreactor of item 53, comprising:
    a base portion having the first chamber;
    an intermediate portion forming at least part of the second, outer chamber and at least part of the third inner chamber; and
    a cover portion for positioning over the intermediate portion.
55. The bioreactor of item 54, wherein the intermediate portion comprises a first support for supporting a first bed of the plurality of stacked beds.
56. The bioreactor of item 54 or item 55, wherein the intermediate portion comprises a second support for supporting a second bed of the plurality of stacked beds.
57. The bioreactor of any of items 54-56, wherein the intermediate portion is adapted for removably connecting with the base portion and the cover portion.
58. The bioreactor of any of items 54-57, wherein the second, outer chamber is bounded by an outer wall, and further including an outer casing forming a space with the outer wall, the space being for insulating, heating, or cooling the second, outer chamber.
59. A bioreactor for culturing cells in connection with a fluid, comprising:
    a first chamber including an agitator for agitating the fluid;
    a second, outer chamber including at least one bed for culturing cells; and
    a third, inner chamber for returning fluid from the second outer chamber to the first chamber,
    wherein the second, outer chamber is bounded by an outer wall, and further including an outer casing forming a space with the outer wall, the space being for insulating, heating, or cooling the second, outer chamber.
60. The bioreactor of item 59, wherein the at least one bed comprises a structured fixed bed.
61. The bioreactor of item 58 or item 59, wherein the structured fixed bed comprises a spiral bed.
62. The bioreactor of item 59, wherein the inner chamber is formed by at least one tube.
63. The bioreactor of item 62, wherein the at least one tube is connected to first and second supports bounding the at least one bed.
64. The bioreactor of item 63, wherein the first and second supports are connected to the outer wall.
65. The bioreactor of item 63 or 64, wherein the first and second supports are at least partially perforated.
66. An apparatus for culturing cells, comprising: a bioreactor including an agitator, the bioreactor adapted for maintaining the agitator in a suspended condition that allows side-to-side movement for alignment with an external drive (which suspended agitator may form part of any of items 1-65).
67. The apparatus of item 66, wherein the bioreactor includes a base portion for receiving the agitator, and an intermediate portion for supporting a carrier for carrying the agitator in the suspended condition.
68. The apparatus of item 67, wherein the carrier comprises a clip for engaging the intermediate portion.
69. An apparatus for culturing cells, comprising:
    a bioreactor including an agitator having a plurality of curved blades (which agitator may form part of any of items 1-68).
70. The apparatus of item 69, wherein the agitator includes a central open region radially inward of the plurality of curved blades.
71. The apparatus of item 69 or item 70, wherein the agitator includes one or more magnets.
72. The apparatus of any of items 69-71, wherein the blades are curved in a radial direction.
73. A bioreactor comprising first and second stacked, structured beds.
74. The bioreactor of item 73, further including a screen engaging both the first and second stacked, structured beds.
75. The bioreactor of item 73 or item 74, wherein the first and second stacked, structured beds comprise spiral beds.
76. A bioreactor including a structured fixed bed forming a central column of the bioreactor.
77. The bioreactor of item 76, wherein the structured fixed bed comprises a spiral bed.
78. The bioreactor of item 76 or item 77, wherein an inner surface of the structured fixed bed is fluid-impervious.

79. A method of manufacturing a bioreactor, comprising:
connecting a base portion including a first chamber with an agitator for agitating a fluid to at least one intermediate portion forming at least portion of a second, outer chamber for culturing cells in connection with fluid transferred from the second, outer chamber, and a third, inner chamber for returning fluid to the first chamber of the base portion.

80. The method of item 79, further including the step of connecting a cover portion over the at least one intermediate portion.

81. The method of item 79 or item 80, further including the step of spirally wrapping a matrix material around the intermediate portion to form a structured fixed bed for culturing cells in the outer chamber.

82. The method of any of items 79-81, further including the step of inserting a structured fixed bed into the second, outer chamber.

83. The method of any of items 79-82, further including providing an outer casing to form a periphery of the second, outer chamber.

84. The method of any of items 79-83, further including the step of connecting the outer casing to the base portion.

85. The method of any of items 79-84, further including the step of stacking a plurality of structured fixed beds in the second, outer chamber.

86. The method of any of items 79-85, further including the step of providing a perforated support between the plurality of structured fixed beds.

87. The method of any of items 79-86 further including the step of suspending the agitator above the base portion in a manner that permits side-to-side movement to align with an external drive.

88. A method of manufacturing a bioreactor, comprising: providing a plurality of structured fixed beds in the bioreactor.

89. The method of item 88, further including the step of providing a perforated spacer between each of the plurality of structured fixed beds.

90. The method of item 88 or 89, further including the step of providing an inner tube along an inner side of each structured fixed bed and an outer tube along an outer side of each structured fixed bed.

91. The method of any of items 88-90, further including the step of providing a casing radially outward of the outer tube, the casing creating a space for insulating, heating, or cooling the bioreactor.

As used herein, the following terms have the following meanings:

"A", "an", and "the" as used herein refers to both singular and plural referents unless the context clearly dictates otherwise. By way of example, "a compartment" refers to one or more than one compartment.

"About," "substantially," or "approximately," as used herein referring to a measurable value, such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, while the bioreactor is shown in a vertical orientation, it could be used in any orientation. It should be understood that various alternatives to the embodiments of the invention described herein may be employed in practicing the invention. It is intended that the following claims define the scope of the protection under the applicable law and that methods and structures within the scope of these claims and their equivalents be covered thereby.

The invention claimed is:

1. A bioreactor for culturing cells in connection with a flow of medium, comprising:
a housing forming an interior compartment, the interior compartment including:
a first chamber having an fluid input end and a fluid output end, the first chamber including a structured fixed bed having at least one spacer layer containing a tortuous path producing structure adjacent to at least two cell immobilization layers for allowing passage of cells and the flow of medium along the surface of the at least two cell immobilization layers and the at least one spacer layer in a tortuous path to create turbulence in the flow of medium to drive the cells into one or more of the at least two cell immobilization layers and adhere at a depth therein;
a second chamber for returning fluid having passed through the structured fixed bed from the fluid input end to the fluid output end of the first chamber, and back to the fluid input end of the first chamber; and
a third chamber for recirculating fluid through the structured fixed bed.

2. The bioreactor of claim 1, wherein the at least one spacer layer and at least two cell immobilization layers are arranged in a spiral configuration.

3. The bioreactor of claim 1, wherein the at least one spacer layer and at least two cell immobilization layers are arranged a stacked configuration.

4. The bioreactor of claim 1, wherein the at least one spacer layer and at least two cell immobilization layers are in direct contact.

5. The bioreactor of claim 1, wherein the at least one spacer layer and at least two cell immobilization layers are concentric.

6. The bioreactor of claim 1, wherein the third chamber includes an agitator located in a container including one or more openings for delivering media flow to the fluid input end of the first chamber.

7. The bioreactor of claim 1, wherein the at least one spacer layer comprises a mesh.

8. The bioreactor of claim 1, wherein the at least two cell immobilization layers comprise a woven material.

9. The bioreactor of claim 1, wherein the structured fixed bed comprises an open central core in which the second chamber is located.

10. The bioreactor of claim 1, wherein the second chamber is radially inward of the first chamber and separated therefrom by an imperforate wall.

11. An apparatus for culturing cells in connection with a flow of medium, comprising:
a bioreactor comprising a housing forming an interior compartment;
a structured fixed bed for culturing cells located in the interior compartment, the structured fixed bed comprising mesh layers allowing passage of cells and the flow of medium along the surfaces of the mesh layers while also creating turbulence in the flow of medium to drive the cells into one or more layers of the structured fixed bed and adhere therein;
an external reservoir and conduits for circulating fluid to the bioreactor.

12. The apparatus of claim 11, wherein the one or more mesh layers of the fixed bed comprise a plurality of layers of woven material in direct contact with one another.

13. The apparatus of claim 12, wherein the plurality of layers of woven material are wound around an imperforate tube.

14. The apparatus of claim 11, wherein the structured fixed bed comprises a stacked configuration.

15. The apparatus of claim 11 wherein the bioreactor comprises a lid connected to the housing, the lid including at least one port to which at least one of the conduits is connected.

16. The apparatus of claim 11, wherein the conduits comprise a first conduit connecting a first port of the bioreactor to the external reservoir and a second conduit connecting a second port of the bioreactor to the external reservoir.

17. A bioreactor for culturing cells in connection with a flow of medium, comprising:
a housing forming an interior compartment, the interior compartment including:
a first chamber comprising a wound structured fixed bed for entrapping cells therein, the first chamber having an fluid input end and a fluid output end; and
a second chamber concentric with the first chamber and defined by an imperforate wall for returning fluid having passed through the structured fixed bed from the fluid input end to the fluid output end back to the fluid input end of the first chamber.

18. The bioreactor of claim 17, wherein the wound structured fixed bed comprises a plurality of layers of material wrapped around the imperforate wall.

19. The bioreactor of claim 18, wherein at least one of the plurality of layers of material comprises a mesh.

20. The bioreactor of claim 17, wherein the housing comprises the imperforate wall and surrounds the wound structured fixed bed.

* * * * *